(12) United States Patent
Hong et al.

(10) Patent No.: US 9,964,541 B2
(45) Date of Patent: May 8, 2018

(54) METHOD AND DEVICES FOR CAPTURING CIRCULATING TUMOR

(71) Applicant: THE BOARD OF TRUSTEES OF THE UNIVERSITY OF ILLINOIS, Urbana, IL (US)

(72) Inventors: Seungpyo Hong, Naperville, IL (US); Ja Hye Myung, Daejeon (KR); David Eddington, Wheaton, IL (US); Cari Launiere, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 0 days. days.

(21) Appl. No.: 15/016,005

(22) Filed: Feb. 4, 2016

(65) Prior Publication Data
US 2017/0254809 A1    Sep. 7, 2017

Related U.S. Application Data

(63) Continuation of application No. 13/265,916, filed as application No. PCT/US2010/032266 on Apr. 23, 2010, now abandoned.

(60) Provisional application No. 61/174,602, filed on May 1, 2009, provisional application No. 61/172,454, filed on Apr. 24, 2009.

(51) Int. Cl.
G01N 33/574    (2006.01)

(52) U.S. Cl.
CPC ................. G01N 33/574 (2013.01)

(58) Field of Classification Search
None
See application file for complete search history.

(56) References Cited

U.S. PATENT DOCUMENTS

| 5,395,609 | A | 3/1995 | Stuttle |
| 5,460,945 | A | 10/1995 | Springer et al. |
| 5,939,404 | A | 8/1999 | Iijima et al. |
| 6,551,843 | B1 | 4/2003 | Rao et al. |
| 6,773,928 | B1 | 8/2004 | Yin et al. |
| 2003/0087292 | A1 | 5/2003 | Chen et al. |
| 2007/0017633 | A1 | 1/2007 | Tonkovich et al. |
| 2007/0026417 | A1 | 2/2007 | Fuchs et al. |
| 2007/0041934 | A1 | 2/2007 | William et al. |
| 2007/0178084 | A1 | 8/2007 | King et al. |

(Continued)

FOREIGN PATENT DOCUMENTS

| WO | WO-2008131301 A1 | 10/2008 |
| WO | WO-2009043057 A2 | 4/2009 |

OTHER PUBLICATIONS

International Preliminary Report on Patentability for International Application No. PCT/US2010/032266, dated Oct. 25, 2011.

(Continued)

*Primary Examiner* — Paul S Hyun
(74) *Attorney, Agent, or Firm* — Marshall, Gerstein & Borun LLP

(57) ABSTRACT

A method of capturing a Circulating Tumor Cell (CTC) from a sample includes introducing a sample into a microfluidic device having a cell capture surface and a flow modification surface under conditions that allow a CTC to bind to a cell rolling-inducing agent and a capturing agent disposed on the cell capture surface. The flow modification surface induces a rotational flow within the sample as it flows through the microfluidic device.

20 Claims, 18 Drawing Sheets

(56) References Cited

U.S. PATENT DOCUMENTS

2008/0124721 A1    5/2008   Fuchs et al.
2008/0199362 A1    8/2008   Chong et al.
2012/0077246 A1    3/2012   Hong et al.

OTHER PUBLICATIONS

International Search Report and Written Opinion for International Application No. PCT/US2010/032266, dated Jan. 3, 2011.
Leckband et al., An approach for the stable immobilization of proteins. *Biotechnol. Bioeng.*, 37(3):227-37 (1991).
Rusmini et al., Protein immobilization strategies for protein biochips. *Biomacromolecules*, 8(6):1775-89 (2007).
Stroock et al., Chaotic mixer for microchannels. *Science*, 295(5555):647-51 (2002).

1. Substrate

2. Apply PDMS Stencil

3. Conjugate EpCAM

4. Remove Stencil

5. Backfill with E-Selectin

G5 (G7) Dendron     Dendron-anti-EpCAM conjugate

Epoxy-coated surface     bifunctional PEG coated surface

METHOD AND DEVICES FOR CAPTURING CIRCULATING TUMOR

CROSS REFERENCE TO RELATED APPLICATION

This application is a continuation of U.S. patent application Ser. No. 13/265,916, filed Oct. 24, 2011 which is the U.S. National Stage of International Application No. PCT/US2010/032266, filed Apr. 23, 2010, which claims priority to U.S. Provisional Patent Application No. 61/172,454, filed Apr. 25, 2009, and U.S. Provisional Patent Application No. 61/174,602, filed May 1, 2009, the disclosures of which are incorporated herein by reference in their entirety.

STATEMENT OF GOVERNMENT SUPPORT

This invention was made with government support under Grant No. CBET-0931472 awarded by the National Science Foundation. The government has certain rights in the invention.

BACKGROUND

Field of the Invention

The invention relates to a method of capturing Circulating Tumor Cells from a sample, and a microfluidic device for performing the method.

Brief Description of Related Technology

Cancer remains one of the world's most devastating diseases, with more than 10 million new cases every year. Although recent advances in diagnostic and therapeutic methods to treat primary tumors have resulted in a decrease in mortality of cancer for the past two years, metastasis of cancer still poses a great challenge as patients often relapse. Disseminated and Circulating tumor cells (DTCs and CTCs, respectively) are known to induce secondary tumor formation at distant sites from primary tumors, known as metastasis. Two major theories describing cancer metastasis, the seed and soil hypothesis and the mechanical trapping theory, are available and the extravasation process for each are similar, consisting of three sequential steps. The metastasis mechanism is known to be initiated by cell rolling the naturally occurring process utilized to recruit leukocytes to sites of inflammation. In the second step, the cells firmly attach to the endothelial cells. In the third step, the cells transmigrate through the endothelium (diapedesis), resulting in secondary tumor formation.

Research efforts on diagnosis and prognosis of metastatic cancer have concentrated on the detection of DTCs in bone marrow (BM) and CTCs in blood. Detection of DTCs requires aspiration of BM—a process that is invasive, time-consuming, and often painful for the patients, precluding repeated samplings that are necessary for prognosis studies along with therapeutic treatments. Consequently, effective detection of CTCs in peripheral blood of cancer patients holds a promise as an alternative due to its minimal invasiveness and easy samplings (i.e. blood drawing). However, the clinical usage of CTCs has not yet been implemented for routine clinical practice. In fact, the clinical significance of CTCs in patient blood is less clear than that for DTCs in BM. Unlike DTCs in BM that are relatively easy to enrich using Ficoll-based assays or the OncoQuick approach, and other immunomagnetic enrichment procedures, CTCs are extremely rare (estimated to be in the range of one tumor cell in the background of $10^6$-$10^9$ normal blood cells), presenting a tremendous challenge for efficient, clinically significant detection of CTCs.

Thus, there exists in the art a need for devices and methods to efficiently isolate circulating tumor cells with enhanced sensitivity and specificity to aid in diagnosis and prognosis of cancer.

SUMMARY OF THE INVENTION

In one aspect of the disclosure, there is provided a method of capturing a circulating tumor cell (CTC) in a sample comprising the step of introducing said sample into a microfluidic device under conditions that allow a CTC to bind to a cell rolling-inducing agent and a capturing agent, the device inducing a rotational flow with the sample, the device comprising an immobilized cell rolling-inducing agent and an immobilized capturing agent.

In one aspect, the method further comprises applying a shear stress between 0.05 dyn/cm$^2$ and 10 dyn/cm$^2$ on the sample introduced into the device.

In another aspect of the method, the shear stress is between 0.1 dyn/cm$^2$ and 2 dyn/cm$^2$.

In yet another aspect of the method, the shear stress is about 0.16 dyn/cm$^2$.

In another aspect of the method, the cell rolling-inducing agent is a selectin or a CTC binding fragment of a selectin. In one aspect, the selectin is selected from the group consisting of E-selectin, P-selectin, and L-selectin.

In another aspect of the method, the capturing agent specifically binds a moiety on a CTC cell surface, the capturing agent selected from the group consisting of an antibody, an antibody fragment, an engineered antibody, folic acid, transferrin, a peptide, and an aptamer. In one aspect, the antibody is anti-EpCAM. In another aspect, the peptide is an RGD peptide.

In one aspect of the method, the capturing agent is immobilized via attachment to a surface of the microfluidic device. In another aspect, the capturing agent is immobilized via attachment to a linker and the linker is attached to a surface of the device. In one aspect, the linker is a polymeric nanolinker. In another aspect, the polymeric nanolinker comprises a modified poly(amidoamine) dendrimer covalently attached to polyethylene glycol. In another aspect, the modified poly(amidoamine) dendrimer is selected from the group consisting of a generation 3, a generation 4, a generation 5, a generation 6, a generation 7, a generation 8, and a generation 9 modified poly(amidoamine) dendrimer.

In another aspect of the method, the polymeric nanolinker comprises polyester-n-carboxylate-1-alkyne dendron covalently attached to polyethylene glycol, wherein n is 8, 16, 32, 64, or 128.

In another aspect of the method, the sample comprises blood.

In another aspect of the method, the immobilized cell rolling-inducing agent and the immobilized capturing agent are arranged in a substantially uniform manner.

In yet another aspect of the method, the immobilized cell rolling-inducing agent and the immobilized capturing agent are arranged in a pattern.

In still another aspect of the method, the cell-rolling inducing agent is covalently attached to a surface of the microfluidic device.

In another aspect of the method, the cell-rolling inducing agent is covalently attached to the surface via a chemical moiety selected from the group consisting of an epoxy group, a carboxyl group, a thiol group, an alkyne group, an azide group, a maleimide group, a hydroxyl group, an amine group, an aldehyde group, and a combination thereof.

In yet another aspect of the method, the cell-rolling inducing agent is immobilized to a surface of the microfluidic device via a linker. In one aspect, the linker is selected from the group consisting of a dendrimer, a dendron, a dextran, polyethylene glycol, poly(L-lysine), poly(L-glutamic acid), polyvinyl alcohol, polyethylenimine, poly(lactic acid), poly(glycolic acid), and a combination thereof.

Also provided herein is a microfluidic device for capturing a circulating tumor cell (CTC) from a sample, comprising a channel comprising a cell capture surface and a flow modification surface, the cell capture surface comprising a cell rolling-inducing agent and a capturing agent immobilized on the cell capture surface, and the flow modification surface comprising one or more ridges extending into the channel and arranged to induce a rotational flow in a sample flowing through the channel.

In one aspect of the device, the cell rolling-inducing agent is a selectin or a CTC binding fragment of a selectin. In another aspect of the device, the selectin is selected from the group consisting of E-selectin, P-selectin, and L-selectin.

In another aspect of the device, wherein the capturing agent is adapted to specifically bind to a moiety on a CTC cell surface, and in various aspects, the capture agent is selected from the group consisting of an antibody, an antibody fragment, an engineered antibody, folic acid, transferrin, a peptide, and an aptamer. In one aspect, the antibody is anti-EpCAM. In another aspect, the peptide is an RGD peptide.

In another aspect of the device, the capturing agent is immobilized on the cell capture surface by direct attachment of the capturing agent to the cell capture surface.

In yet another aspect of the device, the capturing agent is immobilized on the cell capture surface by attachment to a linker directly attached to the cell capture surface. In one aspect, the linker is a polymeric nanolinker. In another aspect, the polymeric nanolinker comprises a modified poly(amidoamine) dendrimer covalently attached to polyethylene glycol. In an another aspect, the modified poly(amidoamine) dendrimer is selected from the group consisting of a generation 3, a generation 4, a generation 5, a generation 6, a generation 7, a generation 8, and a generation 9 modified poly(amidoamine) dendrimer. In another aspect, the polymeric nanolinker comprises polyester-n-carboxylate-1-alkyne dendron covalently attached to polyethylene glycol, wherein n is 8, 16, 32, 64, or 128.

In another aspect of the device, the cell rolling-inducing agent and the capturing agent are arranged in a substantially uniform manner.

In another aspect of the device, the cell capture surface comprises a pattern of first and second regions, the first region comprising the cell rolling-inducing agent, and the second region comprising the capture agent. In one aspect, the first region further comprises the capture agent.

In another aspect of the device, the first and second regions are arranged in an alternating pattern.

In another aspect of the device, the cell-rolling inducing agent is covalently attached to the cell capture surface. In another aspect, the covalent attachment is through a chemical moiety selected from the group consisting of an epoxy group, a carboxyl group, a thiol group, an alkyne group, an azide group, a maleimide group, a hydroxyl group, an amine group, an aldehyde group, and combinations thereof.

In another aspect of the device, the cell-rolling inducing agent is immobilized to a surface of the microfluidic device via a linker. In another aspect, the linker is selected from the group consisting of a dextran, a dendrimer, polyethylene glycol, poly(L-lysine), poly(L-glutamic acid), polyvinyl alcohol, polyethylenimine, poly(lactic acid), poly(glycolic acid), and a combination thereof.

In another aspect of the device, the one or more ridges are angled obliquely relative to the channel.

In still another aspect of the device, the one or more ridges are at a 45 degree angle relative to the channel.

In yet another aspect of the device, the one or more ridges have a linear shape.

In another aspect of the device, the one or more ridges have a herringbone shape.

In another aspect of the device, the one or more ridges are arranged in a pattern. In another aspect, the pattern comprises first pattern regions and second pattern regions disposed between adjacent first pattern regions, wherein the first pattern regions comprise the one or more ridges and the second pattern regions are devoid of ridges. In another aspect, the pattern comprises first and second pattern regions, the first and second pattern regions each comprising one or more ridges, and the ridges in the first pattern region are oriented, sized, and/or shaped differently than the ridges in the second pattern region.

In another aspect of the device, the pattern further comprises a third pattern region disposed between adjacent first and second pattern regions, the third pattern region being devoid of ridges.

In another aspect of the device, the ridges have a height of about 50 µm to about 300 µm.

In another aspect of the device, the ridges have a width of about 50 µm to about 300 µm.

In another aspect of the device, the ridges have a spacing of about 50 µm to about 500 µm.

In yet another aspect of the device, the flow modification surface is disposed opposite the cell capture surface.

In another aspect of the device, the channel has a height of about 50 µm to about 600 µm.

In another aspect of the device, the channel has a width of about 200 µm to about 2000 µm.

Other features and advantages of the present disclosure will become apparent from the following detailed description. It should be understood, however, that the detailed description and the specific examples, while indicating preferred embodiments of the disclosure, are given by way of illustration only, because various changes and modifications within the spirit and scope of the disclosure will become apparent to those skilled in the art from this detailed description.

DETAILED DESCRIPTION OF THE INVENTION

It must be noted that as used herein and in the appended claims, the singular forms "a," "and," and "the" include plural referents unless the context clearly dictates otherwise.

Figure 4:
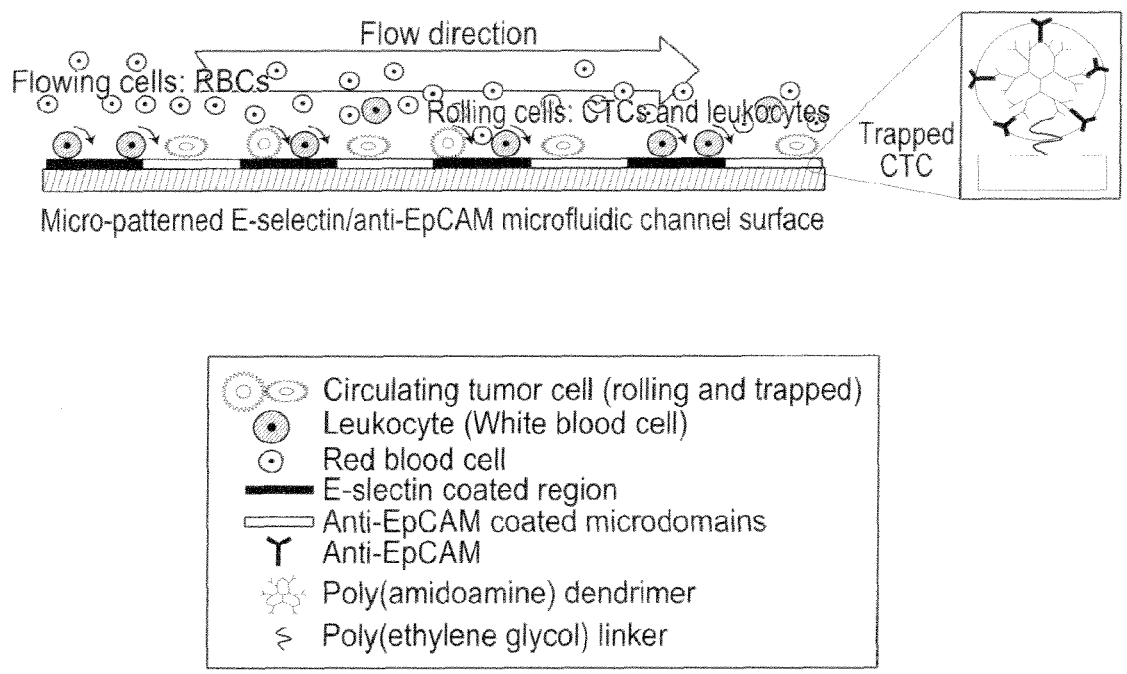
FIG. 4 is schematic diagram of CTC capturing on a cell capture surface using iterative cell rolling (E-selectin: red) and multivalent stationary adhesion (anti-EpCAM: green) in accordance with an embodiment of the disclosure. The inset diagram represents immobilized anti-EpCAM through flexible polymer nanolinkers (dendrimers and PEG: blue) by which the multivalent effect can be achieved through locally concentrated anti-EpCAM. The flow direction appears to be linear for simple illustration but actual flow in the chip will be rotated by the flow modification surface (not shown) disposed in the channel.

In one aspect, a device for capturing circulating tumor cells (CTCs) from a sample includes a channel that includes a cell capture surface 12 and a flow modification surface 20. The cell capture surface 12 includes a cell rolling-inducing agent and a capturing agent 18. The flow modification surface 20 includes one or more structures arranged to induce a rotational flow in the a sample flowing through the channel. Referring to FIG. 4, a method for capturing CTCs from a sample, in one aspect, includes introducing the sample into the device 10 under conditions that allow a CTC to bind to the cell-rolling-inducing agent and a capturing agent 18. The flow modification surface 20 induces a rotational flow in the sample, which may allow for enhanced contact of the cells with the cell capture surface 12, and, thus, for more efficient CTC capture.

The methods of the invention provide for high throughput separation of biological samples in a physiological range of flow rates from about 200 to 500 μL/min. In some embodiments, a shear stress of between 0.05 dyn/cm$^2$ and 10 dyn/cm$^2$ is applied to the sample introduced into the microfluidic device 10. In some embodiments, a shear stress of between 0.1 dyn/cm$^2$ and 2 dyn/cm$^2$ is applied to the sample introduced into the microfluidic device 10. In some embodiments, the shear stress is about 0.05, about 0.10, about 0.15, about 0.20, about 0.25, about 0.30, about 0.35, about 0.40, about 0.45, about 0.50, about 0.55, about 0.60, about 0.65, about 0.70, about 0.75, about 0.80, about 0.85, about 0.90, about 0.95, about 1.0, about 1.1, about 1.2, about 1.3, about 1.4, about, 1.5, about 1.6, about 1.7, about 1.8, about 1.9, about 2.0, about 2.1, about 2.2, about 2.3, about 2.4, about, 2.5, about 2.6, about 2.7, about 2.8, about 2.9, about 3.0, about 3.1, about 3.2, about 3.3, about 3.4, about, 3.5, about 3.6, about 3.7, about 3.8, about 3.9, about 4.0, about 4.1, about 4.2, about 4.3, about 4.4, about, 4.5, about 4.6, about 4.7, about 4.8, about 4.9, about 5.0, about 5.1, about 5.2, about 5.3, about 5.4, about, 5.5, about 5.6, about 5.7, about 5.8, about 5.9, about 6.0, about 6.1, about 6.2, about 6.3, about 6.4, about, 6.5, about 6.6, about 6.7, about 6.8, about 6.9, about 7.0, about 7.1, about 7.2, about 7.3, about 7.4, about, 7.5, about 7.6, about 7.7, about 7.8, about 7.9, about 8.0, about 8.1, about 8.2, about 8.3, about 8.4, about, 8.5, about 8.6, about 8.7, about 8.8, about 8.9, about 9.0, about 9.1, about 9.2, about 9.3, about 9.4, about, 9.5, about 9.6, about 9.7, about 9.8, about 9.9, about 10.0 dyn/cm$^2$. In some embodiments, the shear stress is about 0.16 dyn/cm$^2$.

I. Microfluidic Device

Figure 1:
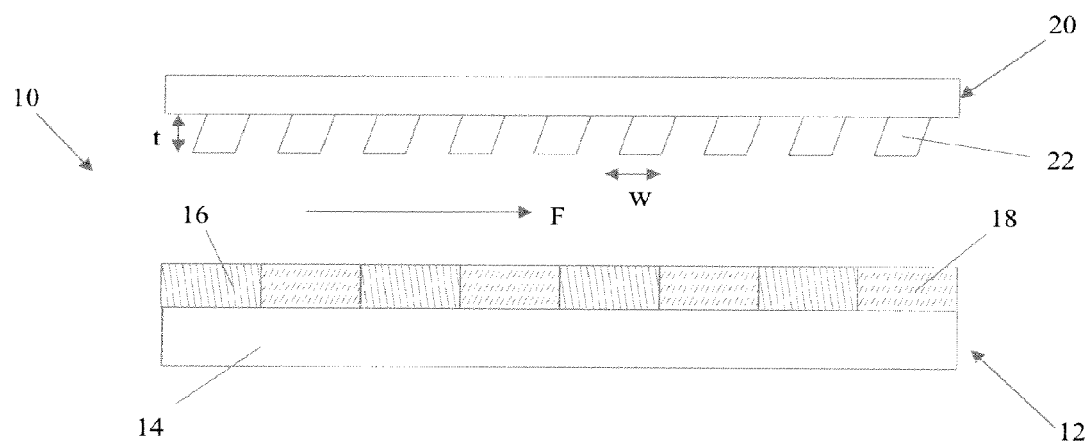
FIG. 1 is a cross-sectional view of a microfluidic device having a cell capture surface and a flow modification surface in accordance with an embodiment of the disclosure.

Referring to FIG. 1, the device 10 includes a channel having a cell capture surface 12 and a flow modification surface 20. The cell capture surface 12 can be disposed opposite the flow modification surface 20. For example, the cell capture surface 12 can be disposed on the bottom surface of the channel and the flow modification surface 20 can be disposed on the top surface of the channel, opposite the cell capture surface 12. Alternatively, the flow modification can be disposed adjacent to the cell capture surface 12. In yet another embodiment, the cell capture surface 12 and the flow modification surface 20 can be incorporated into a single surface. The channel can be, for example, a closed channel having four walls. The cell capture surface 12 and/or the flow modification surface 20 can be disposed on multiple walls of the channel.

The channel can have any suitable cross-sectional shape. For example, the channel can be rectangular, triangular, circular, or elliptical. The dimension of the microfluidic device 10 can be optimized to maximum fluid rotation while minimizing fluid resistance using the following equation:

$$R = \frac{12\mu L}{wh^3}$$

where μ is the kinematic viscosity, L is the channel length, w is the channel width, and h is the channel height.

For example, the channel can have a height of about 50 μm to about 600 μm, about 100 μm to about 500 μm, about 200 μm to about 400 μm. Other suitable heights include, for example, about 50, 100, 150, 200, 250, 300, 350, 400, 450, 500, 550, or 600 μm. The channel can have a width of about 200 μm to about 2000 μm, about 400 μm to about 1500 μm, about 500 μm to about 1000 μm, or about 600 μm to about 800 μm. Other suitable widths include, for example, about 200, 300, 400, 500, 600, 700, 800, 900, 1000, 1100, 1200, 1500, 1600, 1700, 1800, 1900, or 2000 μm. The channel can have a length of about 200 μm to about 5000 μm, about 400 μm to about 4000 μm, about 600 μm to about 2000 μm, or about 800 μm to about 1000 μm. Other suitable lengths include, for example, about 200, 300, 400, 500, 600, 700, 800, 900, 1000, 1500, 2000, 2500, 3000, 3500, 4000, 4500, or 5000 μm.

The cell capture surface 12 includes a cell-rolling inducing agent 16 and a capturing agent 18 attached to a substrate 14. The substrate 14 can be, for example, glass, plastics (or polymer-coated), hydrogels, matrigel, or extracellular matrix (ECM)-coated substrates. The cell-rolling inducing agent 16 and the capturing agent 18 can be immobilized on the substrate 14 either directly or indirectly, using, for example a linker. The cell-rolling inducing agent 16 and the capturing agent 18 can be arranged uniformly across the cell capture surface 12. For example, as illustrated in FIG. 1, the cell capture surface 12 can include alternating regions having the cell-rolling inducing agent 16 and the capture agent. The alternating regions can have substantially the same widths or the widths can vary among the regions. The regions including the cell rolling-inducing agent and the capturing agent 18 can be arranged, for example, as parallel to or at angles relative to the direction of the flow through the channel. For example, the regions can be arranged tangentially to the direction of the flow through the channel.

Flow modification surfaces are well known in the art. Any known flow modification surface 20 can be used. For example, the flow modification surface 20 can include one or more ridges 22, extending from the surface into the channel. The ridges 22 are shaped, sized, and oriented so as to induce a rotational flow in a sample flowing through the channel. The cell capture surface 12 and the flow modification surface 20 can be included on a single surface of the device, for example, by coating the flow modification surface with the cell-rolling inducing agent 16 and the capture agent 18. For example, the ridges 22 can be coated with the cell-rolling inducing agent 16 and the capture agent 18. All or portions of the ridges 22 can be coated. For example, the side walls of the ridges 22 can be coated with the cell-rolling inducing agent 16 and the capture agent 18. The induction of rotational flow in the sample can enhance cell capture efficiency. Cells having low diffusivity will have a tendency to remain the region of the channel at which they enter. For example, hematologic cells have an inherently low diffusivity due to their large diameter. This detrimentally affects the cell capture process when the cells enter the channel distant from the cell capture surface 12. For example, if a blood cell enters the microfluidic channel near the top, it will likely remain near the top as it travels several centimeters along a microchannel, limiting interaction of the cells with biofunctionalized substrates located at the bottom of the channel. The induction of a rotational flow in the sample will force the cells towards the cell capture surface 12, thereby enhancing the contact between the cells and the cell capture surface 12.

The ridges 22 can have any suitable cross sectional shape, such as, for example, rectangular, circular, elliptical, or triangular. The ridges 22 can have a thickness t of about 10 μm to about 300 μm, about 50 μm to about 300 μm, about 100 µm to about 250 µm, or about 150 µm to about 200 µm. Other suitable thicknesses t include about 10, 15, 20, 25, 30, 35, 40, 45, 50, 55, 60, 65, 70, 75, 80, 85, 90, 95, 100, 125, 150, 175, 200, 225, 250, 275, or 300 µm. The ridges 22 can have a width w of about 50 µm to about 300 µm, about 100 µm to about 250 µm, or about 150 µm to about 200 µm. Other suitable widths w include about 50, 75, 100, 125, 150, 175, 200, 225, 250, 275, or 300 µm. The distance between adjacent ridges 22 can be about 50 µm to about 500 µm, about 100 µm to about 400 µm, or about 200 µm to about 300 µm. Other suitable distances include about 50, 100, 150, 200, 250, 300, 350, 400, 450, or 500 µm. The distance between adjacent ridges 22 can be substantially uniform across the flow modification surface 20 or can vary.

Figure 2:
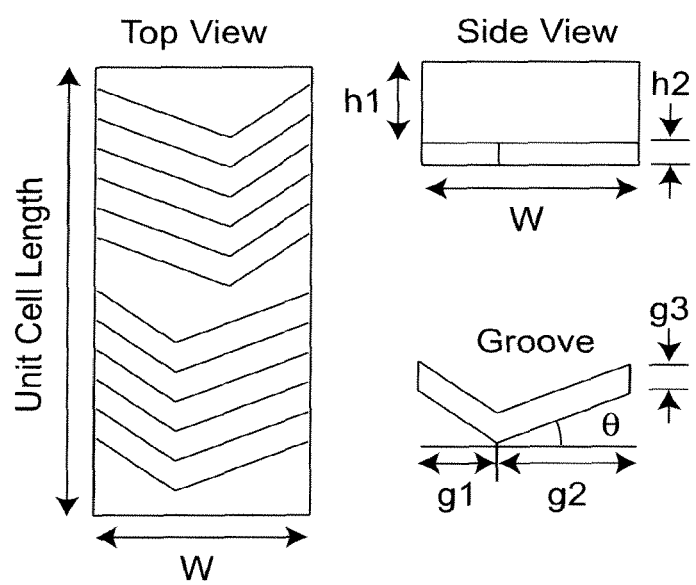
FIG. 2 is a schematic representation of a flow modification surface having a herringbone structure of ridges in accordance with an embodiment of the disclosure.

The ridges 22 can be substantially linear, extending, for example, in a direction perpendicular to the flow. As shown in FIG. 2, the ridges 22 can have a herringbone structure. The ridges 22 can be angled relative to the direction of flow F. For example, the ridges 22 can be angled perpendicularly or obliquely relative to the direction of flow F. In one embodiment, the ridges 22 are at a 45° angle relative to the direction of flow F. Other suitable angles include about 45°, 50°, 55°, 60°, 65°, 70°, 75°, 80°, 85°, 90°, 100°, 110°, 120°, 130°, 140°, 150°, 160° and 170°. The one or more ridges 22 can be angled uniformly. Alternatively, the angle of the ridges 22 can vary across the channel to induce different rotational properties to a sample flowing through the channel.

The one or more ridges 22 can be arranged in a pattern. For example, the flow modification surface 20 can include first regions having the one or more ridges 22 and second regions that are devoid of ridges 22. Alternatively, the second regions can include ridges 22 that are oriented, sized, and/or shaped differently than the ridges 22 of the first regions. The flow modification surface 20 can further include third regions that are completely devoid of ridges 22. Any suitable number of regions having differently sized, oriented, and/or shaped ridges 22 can be included on the flow modification surface 20. The first and second regions can alternate, for example, uniformly across the flow modification surface 20.

The microfluidic device 10 can be fabricated by preparing the cell capture surface 12 with regions having the cell rolling-inducing agent and regions having the capturing agent 18. A microfluidic channel having a flow modification surface 20 can then be attached to the cell capture surface 12.

Figure 3:
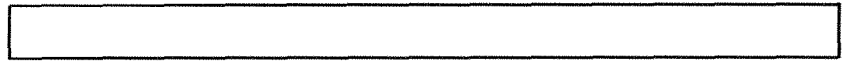
FIG. 3 is a schematic illustration of a method of making a cell capture surface in accordance with an embodiment of the disclosure.
Figure 3:
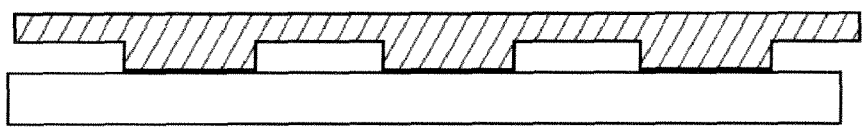
Figure 3:
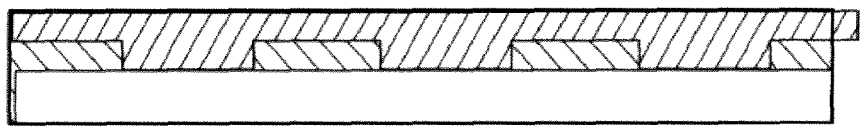
Figure 3:
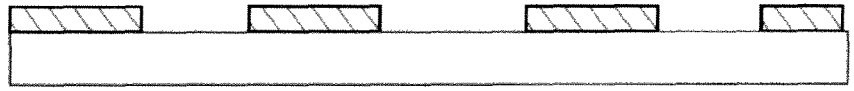
Figure 3:

The cell capture surface 12 can be formed by patterning the cell rolling-inducing agent and the capturing agent 18 on a substrate 14, for example, a glass slide. Any known method of forming regions of a cell rolling-inducing agent and a capturing agent 18 can be used to form the cell capture surface 12. Referring to FIG. 3, the cell rolling-inducing agent and the capturing agent 18 can be patterned, for example, using a polymer stencil, for example, a PDMS stencil. The stencil can be formed as is known in the art, for example, using photolithography. A photoresist can be coated on a wafer and selectively exposed using a photomask. The photoresist is then developed, resulting in unexposed portions of the photoresist being removed, thereby forming a negative mold for the stencil. A polymer, such as PDMS, can then be poured onto the negative mold and cured, thereby resulting in the stencil. The stencil includes one or more structures protruding from a first surface. The size, orientation, and shape of the protruding structures are substantially the same as the size, orientation, and shape of the desired regions of the cell rolling inducing agent and the capturing agent 18. When placed on a substrate 14, the protruding structures function to mask portions of the substrate 14. The cell rolling-inducing agent or the capturing agent 18 can be attached to the unmasked portions of the substrate 14. The stencil can then be removed and the exposed portions of the substrate 14 can be filled with the cell rolling-inducing agent or the capturing agent 18, thereby forming the cell capture surface 12.

The cell rolling-inducing agent and the capturing agent 18 can be attached to the substrate 14 using, for example, physisorption or plasma ablation. For example, the agents can be attached using microfluidic adsorption in which the desired agent is placed in a soluble media and injected through a microfluidic channel placed onto the substrate 14. The solution is allowed to adsorb to the surface over several hours. This technique is advantageous when the desired agents are sensitive to or damaged by heat.

Methods are well known in the art for preparing surfaces with different densities and patterns of suitable groups for covalent bonding (e.g., see Rusmini et al., 8 *Biomacromolecules* 1775-89 (June 2007) and Leckband et al., 37 *Biotechnology and Bioengineering* 227-237 (1991), the entire contents of both of which are incorporated herein by reference). In some embodiments, the density of a capturing agent 18 and/or a cell rolling-inducing agent ranges from about 10 $ng/cm^2$ to about 600 $ng/cm^2$. In some embodiments, the density of a capturing agent 18 and/or a cell rolling-inducing agent is greater than about 30 $ng/cm^2$. For example, in some embodiments, the density of a capturing agent 18 and/or a cell rolling-inducing agent ranges from about 30 $ng/cm^2$ to about 360 $ng/cm^2$. In some embodiments, the density of a capturing agent 18 and/or a cell rolling-inducing agent ranges from about 50 $ng/cm^2$ to about 300 $ng/cm^2$. In some embodiments, the density of a capturing agent 18 and/or a cell rolling-inducing agent ranges from about 100 $ng/cm^2$ to about 200 $ng/cm^2$.

The channel and the flow modification surface 20 can be formed as is known in the art. See Stroock et al., 295 *Science* 647-51, the disclosure of which is incorporated herein by reference in its entirety. The flow modification surface 20 can be formed using soft-lithography. For example, the flow modification surface 20 can be formed using a photoresist, such as a dual height SU-8 photoresist mold. The mold is prepared by first spinning and patterning the microfluidic channel. Before developing the channel pattern, a second photoresist layer is spun onto the mold to generate a pattern for the ridges 22 of the flow modification surface 20. Alignment markers may be added to facilitate proper orientation of the second photoresist layer. The mold is then exposed, hard baked, and developed, thereby resulting in a mold that contains a channel with structures that will cast the ridges 22 of the flow modification surface 20. The resulting mold is then coated with a polymer, for example, PDMS, to form the channel and the flow modification surface 20.

II. Cell Rolling

In some aspects of the disclosure, the microfluidic device 10 comprises an immobilized cell rolling-inducing agent. The formation of transient ligand-receptor interactions occurs commonly between cells flowing in the blood and the vascular endothelium; this physiological process is known as cell rolling. Cell rolling is known to play a key role in biologically important processes such as recruitment of leukocytes to sites of inflammation, homing of hematopoietic progenitor cells after intravenous injection, and CTC-induced metastasis. This behavior is typically mediated by dynamic interactions between selectins (e.g., E-, P-, L-selectins) on the vascular endothelial cell surface and membrane proteins including P-selectin glycoprotein ligand-1

(PSGL-1). A person of skill in the art will recognize that any molecule capable of inducing CTCs to undergo cell rolling can be used to practice the disclosed methods and prepare the disclosed devices.

In some embodiments of the disclosure, the cell rolling-inducing agent is a selectin. In another embodiment, the selectin is endothelial (E)-selectin. In yet another embodiment, the selectin is P-selectin. In another embodiment, the selectin is L-selectin. Moreover, fragments of selectins which retain the ability to bind CTCs are specifically envisioned to be within the scope of the disclosure.

E-selectin (CD62E) is particularly noteworthy in disease by virtue of its expression on activated endothelium and on bone-skin microvascular linings and for its role in cell rolling, cell signaling, and chemotaxis. Many studies point to the key role played by E-selectin in being involved in the adhesion and homing of various types of cancer cells such as prostate, breast, and colon carcinoma cells. E-selectin is synthesized de novo by endothelial cells in response to inflammatory cytokines, such as interleukin-1β (IL-1β) and tumor necrosis factor-α (TNF-α). Thus, cell separation based on the cell rolling behavior is being exploited as it mimics physiological processes and eliminates labeling and label removal steps that are necessary for other immune-labeling detection methods. However, given that a large class of cells, including leukocytes, platelets, neutrophils, mesenchymal and hematopoietic stem cells, and metastatic cancer cells, exhibits rolling on selectins, rolling-based detection for specific cell types from cell mixtures or whole blood has limitations to achieve sufficient specificity, which has hindered translation of the technology to a clinically significant device 10. The methods and devices of the disclosure overcome this limitation by coupling the cell rolling-inducing agent with an immobilized capturing agent 18. Without intending to be bound by any particular theory, it is believed that the cell rolling-inducing agent causes a circulating tumor cell (CTC) to exhibit the "rolling" behavior (described above) on a surface of the microfluidic device 10. The rolling CTC then contacts the immobilized capturing agent 18, and is thereby captured (i.e. immobilized) by the device 10.

Any covalent chemistry may be used to immobilize cell rolling-inducing agents to a surface of the microfluidic device 10. In some embodiments, cell rolling-inducing agents are attached to a surface through one or more chemical moieties. In general, the bond between the chemical moiety and the surface is covalent. Without limitation, in some embodiments, the chemical moiety comprises an epoxy group, a carboxyl group, a thiol group, an alkyne group, an azide group, a maleimide group, a vinyl group, a hydroxyl group, an amine group, an aldehyde group, and combinations thereof.

In some embodiments, the cell-rolling inducing agent 16 is immobilized to a surface of the microfluidic device 10 via a linker. In some embodiments, the linker is selected from the group consisting of a dendrimer, a dendron, a dextran, polyethylene glycol, poly(L-lysine), poly(L-glutamic acid), polyvinyl alcohol, polyethylenimine, poly(lactic acid), poly(glycolic acid), and combinations thereof.

III. Cell Capture

A. Capturing Agent

In some aspects of the disclosure, the microfluidic device 10 comprises an immobilized capturing agent 18. A person of skill in the art will appreciate that any molecule capable of selectively binding to circulating tumor cells will be useful as a capturing agent 18. Specific examples of such molecules exhibiting selective binding to circulating tumor cells include antibodies (or antibody fragments), folic acid, transferrin, certain peptides, and aptamers. Examples of antibodies include, but are not limited to, Trastuzumab (Herceptin), Bevacizumab (Avastin), anti-CD33 antibody (Mylotarg), anti-CD20 antibodies (Zevalin and Bexxar), and their fragments and engineered forms (e.g. diabody, avimer, etc.). Examples of peptides include, but are not limited to, RGD and NGR Epithelial cell adhesion molecule (EpCAM) is frequently overexpressed by a variety of carcinomas such as lung, colorectal, breast, prostate, head and neck, and hepatic origin, but is absent from hematologic cells. Thus, to allow specific binding (i.e. "capturing") of CTCs while avoiding binding of non-CTC cells, in some embodiments, the capturing agent 18 is an anti-EpCAM antibody. Anti-EpCAM antibody is commercially available from several sources including, for example, R&D Systems, Abcam, and Millipore. Alternatively, anti-EpCAM antibodies useful for practicing the methods of the disclosure or generating the devices of the disclosure can be generated by any method known in the art.

As used herein, the terms "antibody" and "immunoglobulin" are understood to mean (i) an intact antibody (for example, a monoclonal antibody or polyclonal antibody), (ii) antigen binding portions thereof, including, for example, an Fab fragment, an Fab' fragment, an (Fab')$_2$ fragment, an Fv fragment, a single chain antibody binding site, an sFv, (iii) bi-specific antibodies and antigen binding portions thereof, and (iv) multi-specific antibodies and antigen binding portions thereof.

As used herein, the terms "bind specifically," "specifically bind" and "specific binding" are understood to mean that the antibody has a selective binding affinity for a particular antigen of at least about $10^6$ M$^{-1}$, more preferably, at least about $10^7$ M$^{-1}$, more preferably at least about $10^8$ M$^{-1}$, and most preferably at least about $10^{10}$ M$^{-1}$. Appropriate controls can be used to distinguish between "specific" and "non-specific" binding.

In some embodiments, the capturing agent 18 is transferrin. Transferrin is an iron binding transport protein, which can bind two atoms of ferric iron in association with the binding of an anion, for example, bicarbonate. Transferrin is responsible for the transport of iron from sites of absorption and heme degradation to those of storage and utilization. The transferrin receptor (TfR) is known to be overexpressed in a broad range of cancers, making transferrin useful as a capturing agent 18.

In some embodiments, the capturing agent 18 is an RGD peptide, a cRGD peptide, RGD mimetics, peptides or proteins containing the RGD sequence, structural or functional equivalents thereof, or combinations thereof. The RGD or RGD mimetics described herein include any peptides or peptide mimetics resulting from the modification of the cyclic Arg-Gly-Asp peptide. The modification can be on the pendant groups and/or on the backbone of the peptide. Peptide synthesis, including the synthesis of peptide mimetics, is well documented and can be readily achieved via, for example, combinatorial chemistry.

In some embodiments, the capturing agent 18 is folic acid. Folic acid is known to bind to a tumor-associated antigen known as the folate receptor (FR), making folic acid useful as a capturing agent 18.

B. Multivalent Effect

Multivalent interactions—the simultaneous binding event of multiple ligands to multiple receptors in biological systems—have been extensively investigated to promote targeting of specific cell types. These activities are also central to a number of pathological processes, including the attachment of viral, parasitic, mycoplasmal, and bacterial pathogens. Studies with biological multivalent inhibitors have yielded quantitative measurements of binding avidities, with increases on the order of 1 to 9 orders of magnitude.

In some aspects of the disclosure, the multivalent effect is accomplished by immobilizing the capturing agent 18 on the substrate 14 of the cell capture surface 12 via attachment to a linker, which is directly attached to the substrate 14 of the cell capture surface 12. In some embodiments, the linker is a polymeric nanolinker. In some embodiments, the polymeric nanolinker is a modified poly(amidoamine) (PAMAM) dendrimer.

The nanolinker may be a dendritic polymer. Any of the known dendritic architectures may be used, including, for example, dendrimers, tecto-dendrimers, regular dendrons, dendrigrafts, and hyperbranched polymers. Dendritic star-branched polymers having a plurality of arms emanating from a nucleus may also be used. Accordingly, as used herein, dendritic polymers are polymers with densely branched structures having a large number of terminal reactive groups. A dendritic polymer includes several layers or generations of repeating units, usually referred to as branch cells, which all contain one or more branch points. Dendritic polymers, including dendrimers and hyperbranched polymers, are prepared by reaction of monomeric units having two or more reactive groups, or a combination of monomeric units in which at least one of the monomeric units has at least three reactive groups. The dendrimers which can be used include those comprised of a plurality of dendrons that emanate from a common core which can be a single atom or a group of atoms. Each dendron generally consists of terminal surface groups, interior branch junctures having branching functionalities greater than or equal to two, and divalent connectors that covalently connect neighboring branching junctures.

Methods of preparing and characterizing dendrimers, dendrons, hyperbranched polymers, star-branched polymers, dense star-branched polymers and hypercomb-branched polymers are all well known in the art and thoroughly described in the literature. Dendrons are regular-branched polymeric molecules and their structures can be precisely controlled at the molecular level and they have unique properties. They are wedge-shaped and comprise a focal point from which the branches originate. Different dendrons may have different numbers of branches extending from each branch and different numbers of layers. In some embodiments of the disclosure, the polymeric nanolinker comprises polyester-n-carboxylate-1-alkyne dendron covalently attached to polyethylene glycol, wherein n is 8, 16, 32, 64, or 128.

Specific examples of dendritic polymers that may be used include poly(amidoamine) (PAMAM) dendrimers, dendrigrafts and hyperbranched polymers; poly(benzylether) dendrimers, dendrigrafts and hyperbranched polymers; polyester dendrimers and hyperbranched polymers; poly(propyleneimine) (PPI) dendrimers, dendrigrafts and hyperbranched polymers; organo silicon-containing dendrimers, dendrigrafts and hyperbranched polymers, polystyrene arborescent polymers.

PAMAM dendrimers have been reported to be an excellent mediator for facilitated multivalent effect because the geometry of the dendrimer preorganizes the ligands into a small region of space as compared to what is obtained if one conjugates the ligands to a similar molecular weight linear polymer. Thus, one has "prepaid" the entropy penalty for localizing the ligands. Second, the dendrimer structure allows all ligands to address the cell surface. This is not necessarily the case for a similar molecular weight hyperbranched polymer in which tangled or cross-linked chains may prevent the needed ligand orientation. PAMAM dendrimers are quite flexible and easily deform from the spherical shape adopted in isotropic media to a disc-like structure upon interaction with a surface. This combination of preorganization, polymer backbone topology, and easy deformability, makes the PAMAM dendrimer an effective material for achieving multivalent binding to cell surfaces. Furthermore, the multivalent effect can significantly increase specificity and sensitivity of detection of target proteins or cells. By immobilizing PAMAM dendrimers conjugated with cancer cell specific markers such as anti-EpCAM, specificity and sensitivity of the surface is substantially increased by the multivalent effect.

In some embodiments, the PAMAM dendrimer is covalently attached to polyethylene glycol.

In some embodiments, the PAMAM dendrimer is selected from the group consisting of a generation 3 PAMAM dendrimer, a generation 4 PAMAM dendrimer, a generation 5 PAMAM dendrimer, a generation 6 PAMAM dendrimer, a generation 7 PAMAM dendrimer, a generation 8 PAMAM dendrimer, and a generation 9 PAMAM dendrimer.

EXAMPLES

The following examples are provided for illustration and are not in any way to limit the scope of the invention.

Example 1: Multivalent Effect

The recent development of nanotechnology has demonstrated many breakthroughs in a range of biomedical applications—particularly for cancer treatment. For a new design of effective targeted drug delivery/imaging vectors based on nanotechnology, multivalent effects are desirable as they dramatically enhance active targeting efficacy. The similar enhancement can be also achieved in specific capturing when the delivery vectors are immobilized on the surfaces.

Preparation of PAMAM dendrimer-based nanodevice: The PAMAM dendrimer-based folate receptor (FAR) targeting nanodevices were synthesized as summarized in FIG. 3. Briefly, G5 PAMAM dendrimers were partially acetylated (70 of the 110 total primary amines), resulting in G5-Ac70. The remaining 40 primary amine groups were used for reaction to further functionalize the dendrimers. Note that a G5 PAMAM dendrimer molecule has approximately 110 primary amine termini according to the previous titration measurement. To fluorescently label the dendrimers, AlexaFluor® 488 (AF488, Molecular Probes) dissolved in DMSO was added to the dendrimer/H2O solution at a molar ratio of 5:1 (AF488:dendrimer) in the presence of 1 M NaHCO 3 and the reaction mixture was stirred at RT for 48 hr. The resulting mixture of the dendrimer conjugate (G5-$Ac_{70}$-AF488) was then dialyzed in water for 2 days and lyophilized for 2 days, followed by 10 cycles of ultrafiltration with PBS (with $Ca^{2+}$ and $Mg^{2+}$) and water using a 10,000 molecular weight cut-off membrane at 21° C., 5000 rpm for 30 min each. G5-Ac 70-AF488 conjugate in $H_2O$ was then reacted with FA preactivated by 1-[3-(dimethylamino)propyl]-3-ethylcarbodiimide/HCl (EDC) in DMF/DMSO at different molar ratios (3:1, 6:1, 9:1, 12:1, 15:1) of FA to G5-$Ac_{70}$-AF488. The same purification process was carried out as described in the AF488 conjugation. Lastly, full acetylation of the remaining primary amine group was completed, yielding our final products G5-Ac-AF488-$FA_0$, G5-Ac-AF488-FA$_{2.6}$, G5-Ac-AF488-FA$_{4.7}$, G5-Ac-AF488-FA$_{7.2}$, G5-Ac-AF488-FA$_{11.5}$, and G5-Ac-AF488-FA$_{13.7}$. Since all the nanodevices were conjugated with the same number of AF488, differences in fluorescence intensities from the nanodevices in later FACS data (FIG. 4a—red squares) can be regarded as a result of differences in nanodevice binding and/or uptake by KB cells. The nanodevices become more polydisperse and ultimately give a bimodal distribution as the number of attached FA increases. In the case of G5-Ac-AF488-FA$_{13.7}$, the polydispersity index (PDI=M$_w$/M$_n$) is 12.41 which is significantly greater than PDIs of previously reported dendrimer conjugates.

Quantitative analysis of multivalent effect mediated by PAMAM dendrimers: The material properties required for maximal multivalent effects include: 1) flexibility for conformational deformation to increase interacting surface area at a low cost of entropy and 2) localized reactive groups for targeting agents to utilize receptor clustering effect for a maximal number of simultaneous binding events in the given area. A series of experiments to quantitatively measure the multivalent targeting has been conducted using PAMAM dendrimers that satisfy the two pre-requisite properties, yielding a substantial enhancement in binding avidity as high as ~170,000 fold compared to the monovalent binding counterpart. To study the interaction of FA-conjugated G5 PAMAM-based nanodevices (G5-Ac-AF488-FAx: x=2.6, 4.7, 7.2, 11.5, or 13.7) with folate binding protein (FBP), the surface plasmon resonance (SPR) technique using BIAcore X (Pharmacia Biosensor AB, Uppsala, Sweden) was employed. FBP was immobilized on the sensor chip surface (channel 2) of a carboxylated dextran-coated gold film (CM 5 sensor chip) by amine coupling as described. The dendritic nanodevices (30 µl) were injected at concentrations of 500 nM, 1 mM, and 2 mM at a flow rate of 10 µl/min, allowing the nanodevices to flow in both channels (channel 1 for reference and channel 2 with FBP) for 3 min. The final SPR sensorgrams were obtained from the signals from channel 2 subtracted by those from channel 1. Binding parameters of free FA with FBP were evaluated by the same condition but at different concentrations (1 and 2 mM used for free FA). The binding curves were fit using the 1:1 Langmuir binding model in BIAevaluation software. Associations and dissociations were fit separately since there was turbulence in the curves between association and dissociation phases in the process of subtracting signals from the reference channel. Dissociation constants (K$_D$) for each dendrimer were obtained by averaging at least three different sets of results which had $\chi^2$ values lower than 3.0. All runs were independently analyzed for errors associated with mass transport by exporting the data files to Excel and plotting dR/dt versus R following the analysis described by Glaser.

To compare the SPR results to in vitro cell level data, the KB cell line (ATCC, Manassas, Va.) was employed and grown continuously as a monolayer at 37° C. and 5% CO$_2$ in RPMI 1640 medium (Mediatech, Herndon, Va.) supplemented with penicillin (100 units/ml), streptomycin (100 mg/ml), and 10% heat-inactivated fetal bovine calf serum (FBS) before use. KB cells were also cultured in RPMI 1640 medium without folic acid (Mediatech) for at least 4 days before experiments, resulting in the folic acid receptor overexpressing KB (FAR$^+$ KB) cell line. For the FACS measurements, the FAR-KB cells were seeded on a 24-well plate for tissue culture at a concentration of 2×10$^5$ cells/well and at 37° C., 5% CO2 for 24 hr. The cells were then incubated with the series of the prepared nanodevices at 37° C. for 1 hr. After removal of supernatants, cells were trypsinized and collected into FACS tubes, followed by centrifugation at 1500 rpm for 5 min to obtain cell pellets. The pellets were washed with PBS (Ca$^{2+}$, Mg$^{2+}$) twice using a repetitive centrifugation and resuspension process and then finally resuspended in PBS with 0.1% bovine serum albumin. The FACS sample preparation was performed on ice to inhibit cellular reactions such as further uptake. Fluorescence signal intensities from the samples were measured using a Coulter EPICS/XL MCL Beckman-Coulter flow cytometer, and data were analyzed using Expo32 software (Beckman-Coulter, Miami, Fla.).

As shown in FIG. 4a, an optimum number of targeting molecules (folic acid (FA)) appeared to be ~5 where the dendrimers showed an exponential increase in binding avidity and sustained their monodispersed properties. Note that conjugation of more than 10 FA molecules caused substantial deterioration of homogeneity of the materials. Based on this optimized design criteria, engineered dendritic anti-cancer nanodevices utilizing the multivalency have exhibited great efficacy in targeting and killing cancer cells both in vitro and in vivo without apparent harmful side effects. This study supports the idea that nanoparticle based drug delivery systems can be significantly improved in targeting efficacy if the optimization process is conducted to maximize the multivalent effect without compromising the material's properties.

The significance of these results regarding the multivalent effect is three-fold: 1) the ability of PAMAM dendrimer-based scaffolds to afford a functional multivalent effector system is demonstrated 2) the in vivo effect is demonstrated to arise from the substantial enhancement of K$_D$, not an increased rate of endocytosis and 3) the on-rate, k$_a$, increases linearly with the number of targeting agents and shows no cooperativity whereas the off-rate, k$_d$, decreases exponentially with the number of targeting agents (4b).

Although the experiments on the multivalent effect are focused on the targeted drug delivery, the results of enhanced binding avidity as high as 170,000 fold clearly indicates that this naturally occurring effect can substantially enhance device sensitivity that is highly desirable for detection and isolation of extremely rare cells such as CTCs. Furthermore, the multivalent effect (exponential increase in binding avidity) appeared to be primarily due to the exponential decrease in dissociation rate constants (FIG. 4b), indicating that capturing efficiency of the multivalent capturing device will be enhanced as the CTCs will likely remain adhered on the surface even at high flow rates (>200 µL/min).

Example 2: Controlled Immobilization of P-Selectin

Covalent immobilization of biologically active species has a number of advantages such as controlling the density, conformation, and enhanced stability of the species. Although covalent immobilization procedures for peptides and enzymes have been extensively studied for decades, covalent immobilization of large molecular weight biomolecules such as selectins present significant challenges due to the increase of binding to non-specific sites and due to the requirement for mild processing conditions to prevent protein inactivation. Given that preparation of devices proposed in this work requires a high level of control over the selectin presentation on surfaces, it is desirable to control density and conformation of selectin, and to introduce controlled co-immobilization capacity for secondary molecules that facilitates selective separation of target CTCs. We have developed covalent immobilization chemistries along with a set of appropriate analytical tool in order to achieve stable and tunable adhesive properties of surfaces with minimal batch-to-batch variations.

Figure 5:
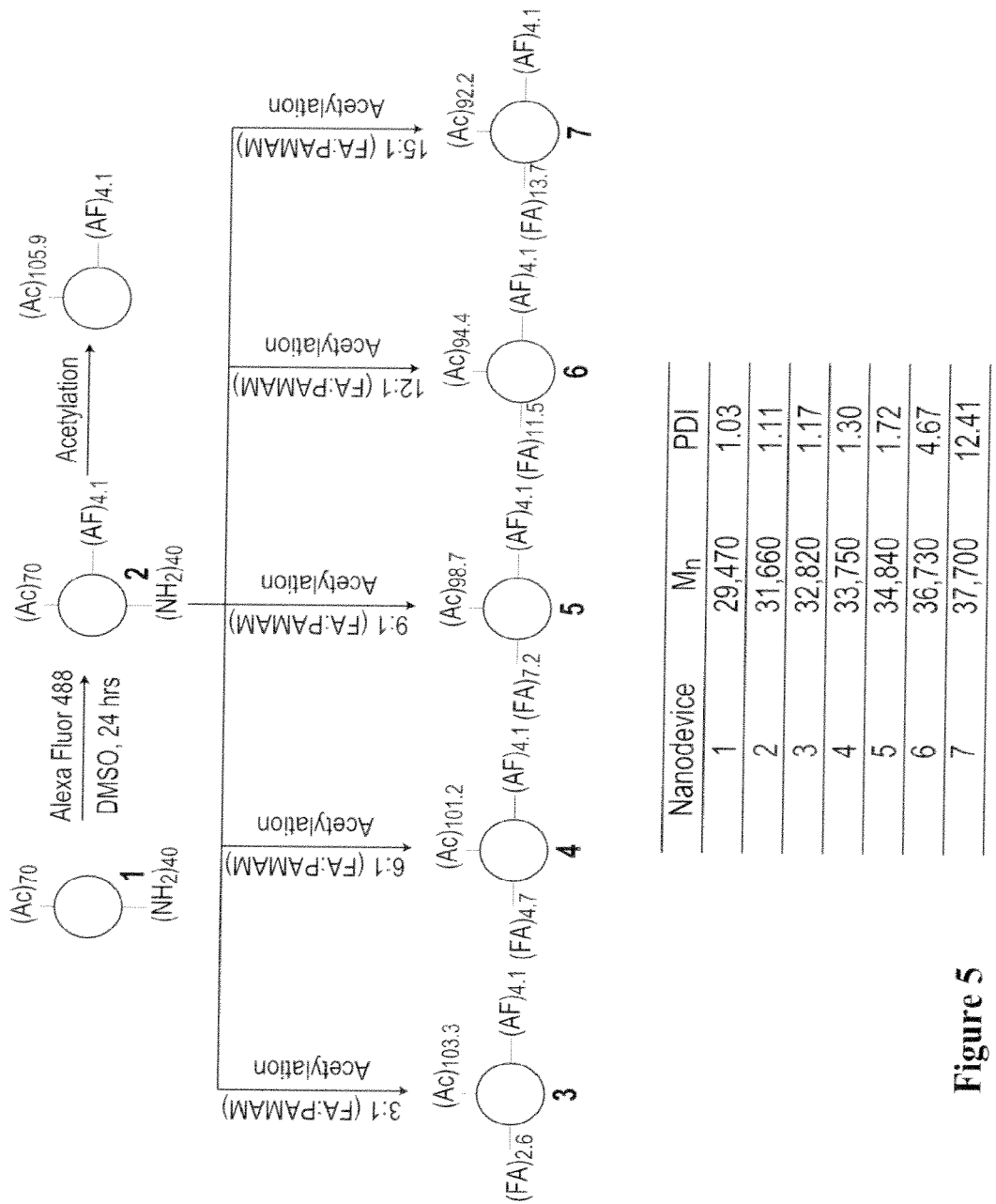
FIG. 5 illustrates a synthetic scheme for G5 PAMAM dendrimer-based nanodevices with AF488 and different numbers of FA molecules. The number average molecular weights and PDIs were determined by GPC. All numbers of functional attachment were calculated from GPC results. The total number of end groups (110) was determined by potentiometric titration.

Enhanced controllability of surfaces by covalent immobilization: Previously, we have shown the surfaces with covalently immobilized P-selectin present enhanced functional stability by approximately 10 times, as compared to those with physisorbed P-selectin. The surface stability was assessed using cell-mimicking microspheres as well as live neutrophils. We also developed immobilization chemistries (as shown FIG. 5) on gold coated, non-folding PEGylated surfaces to employ the flow-based SPR technique that quantitatively analyze the surface functions, offering: 1) easy surface functionalization using thiol chemistries due to the presence of a gold layer and 2) quantitative and real time monitoring of binding events without any modification of analytes. Thus, the SPR technique is useful particularly for determining controllability of density and orientation of P-selectin. The chemistries described in FIG. 5 were developed to achieve non-fouling surfaces and to provide reactive sites for subsequent P-selectin immobilization using oligo (ethylene glycol)-alkanethiols (Prochimia, Poland) on gold coated SPR chips. Briefly, the gold chip surface was cleaned before the subsequent formation of mixed self assembled monolayers (SAMs) by washing with absolute ethanol and drying by nitrogen blowing. SAMs were formed by soaking gold coated substrates in a solution containing a 100 μM total OEG-alkanethiol concentration in ethanol at RT overnight. Following mixtures of different OEG-alkanethiols were used at the indicated molar ratios: OEG-COOH (or —NH 2):OEG-OH (1:39, 1:9, 3:7, 5:5) and OEG-biotin:OEG-OH (1:9). All the SAMs were then rinsed extensively with water and ethanol, followed by drying in a stream of nitrogen. All the buffers and solutions were degassed under vacuum for 30 min before applied into the SPR system. P-selectin was immobilized onto the surface of the mixed SAMs as follows. The chemistry used for the mixed SAMs of OEG-COOH/OEG-OH (FIG. 5a), 10 mM phosphate buffer (PB) was first flowed into a chip at a flow rate of 50 μL/min for 5 min. A 1:1 (v/v) mixture of EDC at 76.68 mg/mL and NHS at 11.51 mg/mL was injected to activate carboxyl groups on the SAMs for 10 min. After flowing for 5 mM P-selectin at a concentration of 20 μg/mL in PB was injected and flowed to be immobilized for 7 min. The chip surface was then washed with PB for 5 min, followed by ethanolamine (100 mM in PB) to inactivate remaining active ester groups and to remove loosely hound P-selectin from the surface. For P-selectin immobilization on the mixed SAM of OEG-biotin/OEG-OH (FIG. 5b), P-selectin was first biotinylated using maleimide-PEO$_2$-biotin (Pierce) before the SPR measurement as shown in FIG. 5. A solution of P-selectin at 50 μl of 1 mg/ml P-selectin in PBS was mixed with 50 molar excess maleimide-PEG 2-biotin solution at 4° C. overnight. The reaction mixture was purified by 4 cycles of ultrafiltration using a 10K molecular weight cut-off membrane. Each cycle was performed at 14,000×g for 30 min. The mixed SAM of OEG-biotin/OEG-OH was mounted on the SPR and 10 μg/mL streptavidin in PBS was flowed for 10 min to create binding sites for the biotinylated P-selectin. P-selectin was then immobilized under the same condition used for other mixed SAM surfaces via strong biotin/avidin binding. For the mixed SAM of OEG-NH$_2$:OEG-OH (FIG. 5c), the surface was first immersed in a solution of sulfosuccinimidyl 4-(N-maleimidomethyl)cyclohexane-1-carboxylate (sulfo-SMCC, Pierce, Rockford, Ill.) at room temperature for 1 hr to convert the amine groups to maleimide groups that specifically binds to a cysteine residue in P-selectin. The chip was mounted on the SPR sensor and PB and PBS were sequentially flowed into the channels. P-selectin was immobilized under the same conditions.

Figure 6:
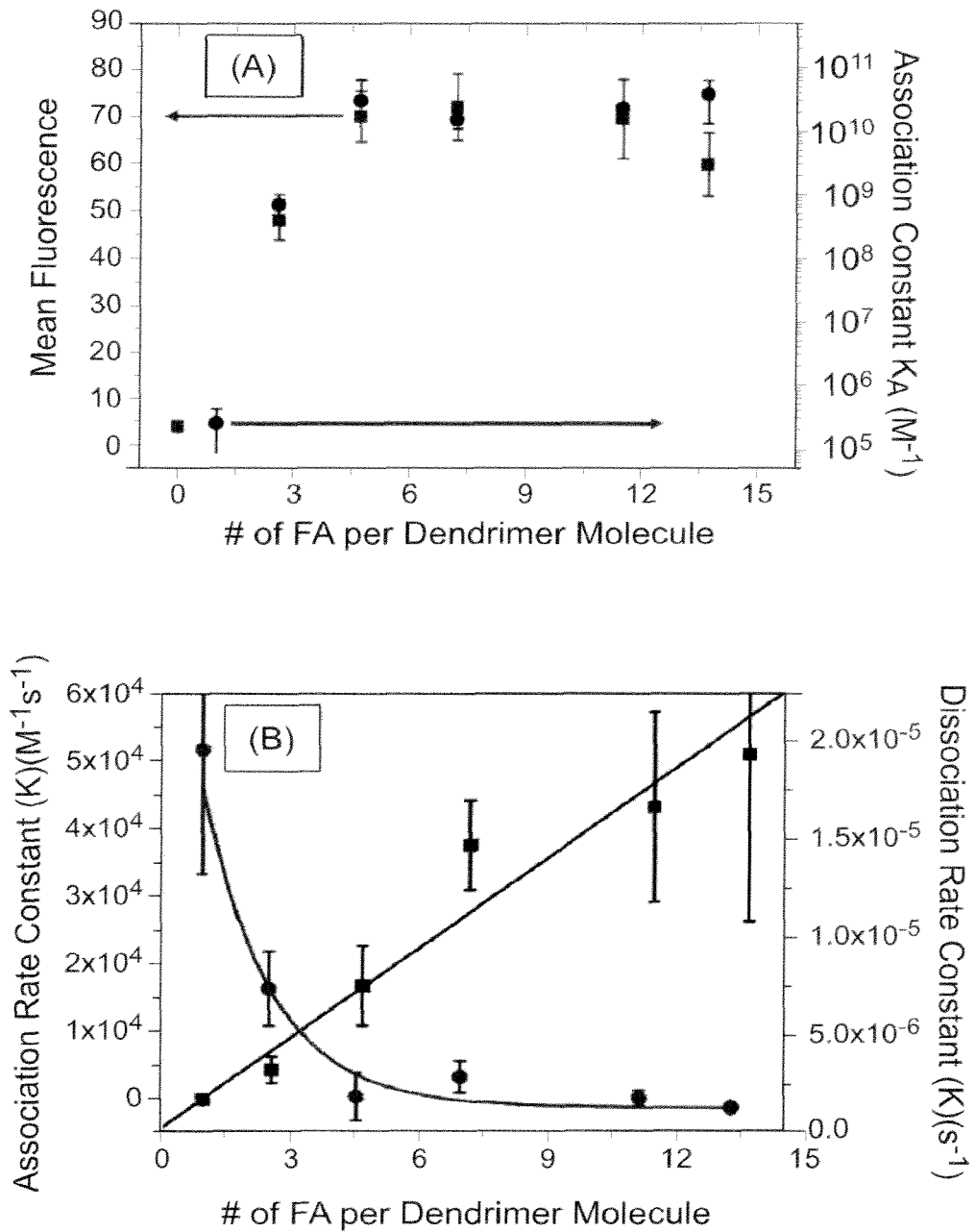
FIG. 6 illustrates a) a comparison of effect of the number of FA per dendrimer molecules between model study using SPR (blue) and in vitro study using FACS (red). The nanodevice with 2.6 FA shows a lower degree of cellular binding and association constant ($K_a$) than the rest of the nanodevices. FACS data were obtained after incubation with dendritic nanodevices with FAR over-expressing KB cells at 37° C. for 1 hr and were averaged from 12 different samples at each condition. Those of association constants were averaged values from at least three runs of the SPR measurements for each point. The association constant ($K_A=1/K_D$) is plotted in this case as it provides the best visual comparison to the FACS data. b) Association rate constant ($k_a$)($M^{-1}$ $s^{-1}$) and dissociation rate constant $k_d$ ($s^{-1}$) of dendrimers with varying numbers of folic acid as measured by SPR. The $k_a$ value increases linearly with the number of folic acids per dendrimer whereas the $k_d$ value decays exponentially with the increasing number of folic acid ligands.
Figure 7:
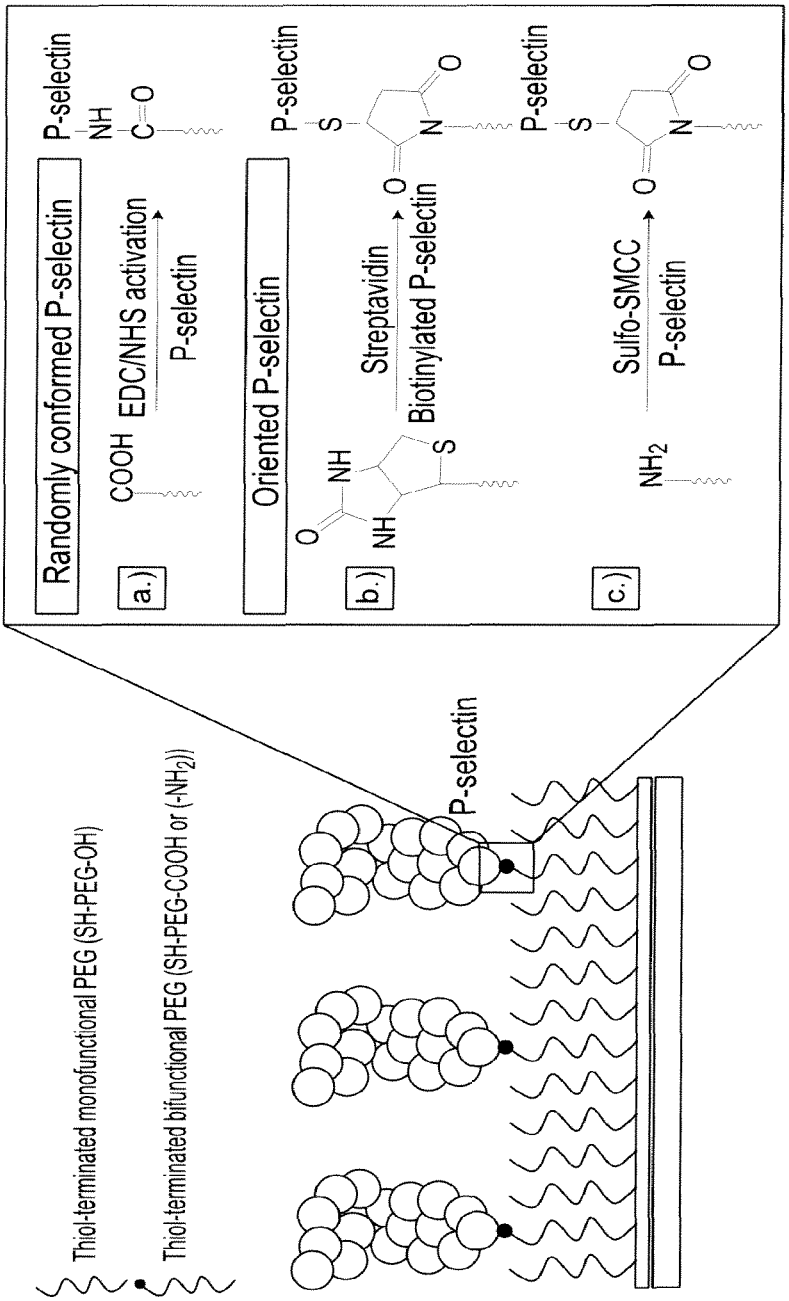
FIG. 7 is a schematic of covalent immobilization of P-selectin on PEG functionalized surfaces using various chemistries.
Figure 8:
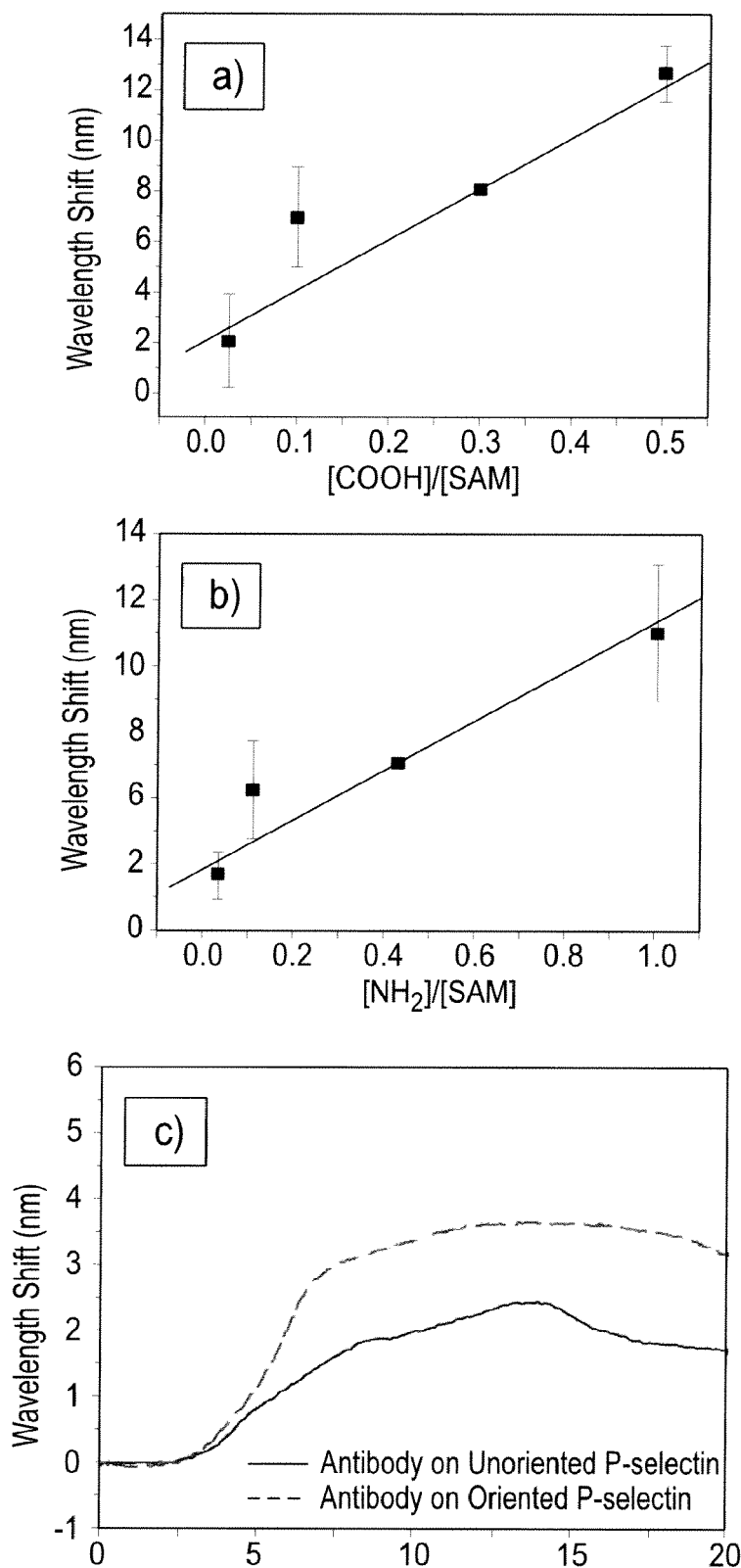
FIG. 8 are a) and b) SPR sensorgrams of density controlled P-selectin immobilization. As shown in a) and b), by changing the ration between OEG-COOH (OEG-NH$_2$) and OEG-OH, the amount of P-selectin immobilized is controlled by wavelength changes up to 20 nm (corresponds to ~300 ng/cm$_2$ of immobilized protein) and is proportional of the content of bifunctional OEGs. c) Effect of P-selectin orientation in antibody binding response on the unoriented P-selectin (using OEG-COOH, FIG. 7a) and oriented P-selectin (using OEG-biotin, FIG. 7b). For this binding curve, two chips with the same amount of immobilized P-selectin were used.

FIGS. 6a and b show that the amount of P-selectin was successfully controlled by varying mixture ratios of the SAM components. The amount of immobilized P-selectin was proportional to the amount of —COOH (or —NH$_2$) containing SAM component in a linear fashion. This results also suggest that the OEG based SAMs reduce non-specific adsorption of P-selectin because only the OEG-COOH or —SH groups on SMCC provides reactive sites for —NH$_2$ or —SH residues in P-selectin, respectively. Orientation effect of P-selectin was also examined by comparing the two different chemistries in FIG. 5a (random conformation) and FIG. 5b (oriented conformation). Because a P-selectin molecule has many amine groups that can react with —COOH groups on the surface, conformation of P-selectin ought to be random. In contrast, P-selectin is known to possess only one cysteine as its 766$^{th}$ amino acid (P-selectin used in this study is composed of 1-771 amino acids of its natural form) on the other side of active binding sites at N terminal. The pre-biotinylation step involves a chemical reaction between the thiol group on P-selectin and the maleimide group on the linker and thus there should be only one biotin per P-selectin molecule, resulting in oriented conformation of P-selectin immobilized through following biotin-streptavidin binding. For channels prepared using the both chemistries, comparable amounts of P-selectin were first immobilized (~12 nm in wavelength shift), followed by flowing 20 μg/mL P-selectin antibody (eBioscience) at a flow rate of 20 μL/min. As a result, the channels with oriented P-selectin exhibit a significantly greater binding response than that from the channels with randomly immobilized P-selectin (FIG. 6c), indicating that orientation of P-selectin was controlled by utilizing thioether chemistry.

Example 3: Rolling Assays of a Tumor Cell Line as a CTC Model

Figure 9:
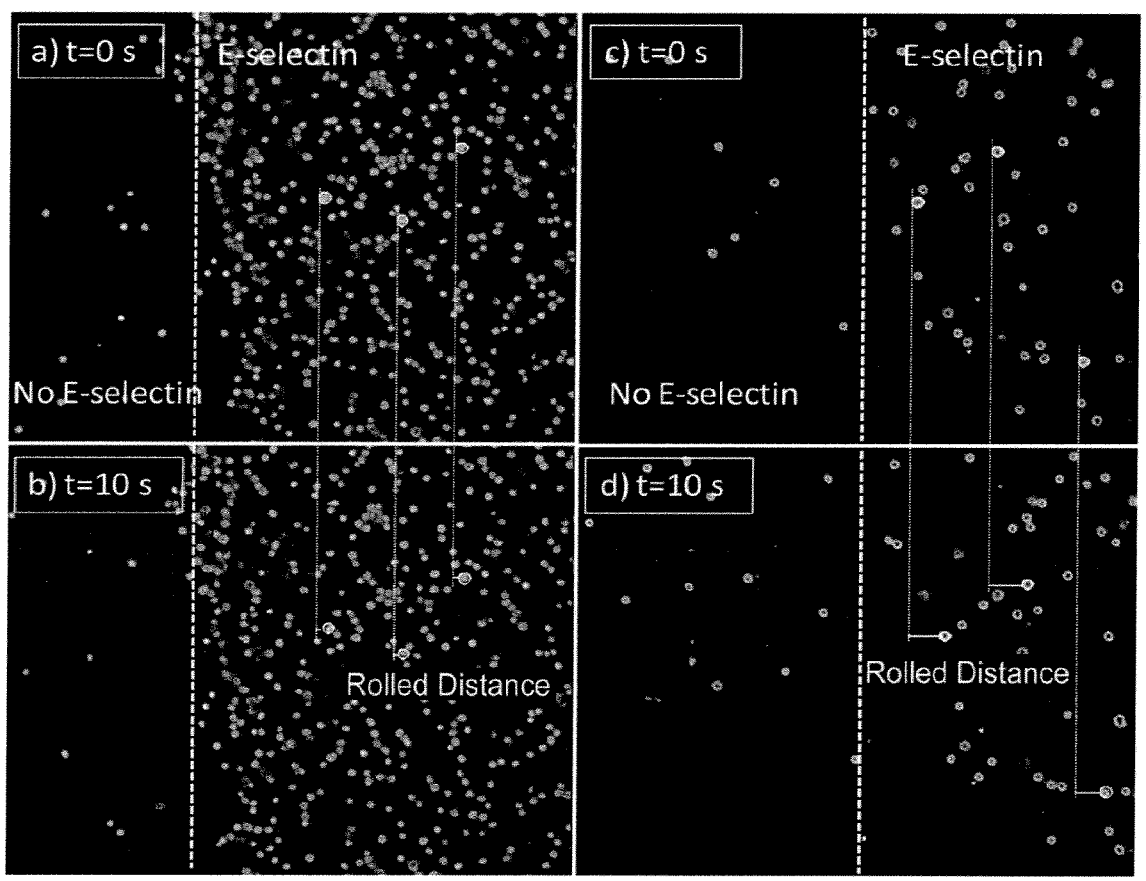
FIG. 9 are time-course images of HL-60 cells (a) and b)) and MCF-7 cells (c) and d)) on the surfaces coated with E-selectin. Both cell lines exhibit the rolling behavior in an E-selectin specific manner. The rolling velocities of HL-60 and MCF-7 cells were 2.12±0.15 and 4.24±0.31 µm/sec at a shear stress of 0.32 dyn/cm2, respectively.

Patterning of E-selectin on a glass substrate: Recombinant human E-selectin chimera (R&D systems, Minneapolis, Minn.) was patterned on an epoxy functionalized glass surface (SuperEpoxy®, ArrayIt Inc, Sunnyvale, Calif.) using a silicone gasket to block a part of the glass substrate during E-selectin immobilization, resulting in the clear interface between E-selectin coated and uncoated regions as shown in FIG. 9 (the yellow dotted lines). An 1.5 cm×6 cm silicone gasket was placed on a SuperEpoxy® glass slide, along with a small piece (0.3 cm×1 cm) of silicone in the center of the slide. The larger gasket was filled with PBS to rinse the surface, followed by incubation with 5 μg/mL E-selectin at RT overnight. The slide was then rinsed with PBS, the small piece was removed, and the entire surface was blocked with 1% BSA solution.

Cell rolling of tumor cells on E-selectin: The rolling response of tumor cells on E-selectin coated surfaces was assessed using a commercially available rectangular parallel-plate flow chamber (Glycotech, Gaithersburg, Md.). A breast cancer cell line MCF-7 (ATCC, Manassas, Va.) was employed as a CTC model. The rolling behavior of the MCF-7 cells was compared with that of HL-60 cells, a human myeloid cell line that expresses high levels of sialyl Lewisx and exhibits rolling on selectins mediated primarily by PSGL-1. With no expression of PSGL-1, MCF-7 cells express CD24 that interacts with selectins and that has been known to be a marker for a subpopulation of MCF-7 cells with higher potential to cause metastasis than CD24-MCF-7 cells. For the flow experiments, the flow chamber with a gasket with thickness of 250 µm and length of 6 cm was placed on the E-selectin coated surface. HL-60 and MCF-7 cells at a 2-8×105 cells/mL concentration were perfused into the chamber at shear stresses of 0.08 and 0.32 dyn/cm2 using a syringe pump (New Era Pump Systems, Inc., Wantagh, N.Y.). During each experiment, flow was interrupted for 1 min, followed by image recording for 2 min at 1 fps image capturing. The average velocities were obtained by averaging rolling velocities of at least 40 cells.

FIG. 9 shows video frames of HL-60 and MCF-7 cells on an E-selectin coated surface at t=0 and 10 sec. The both HL-60 and MCF-7 cells exhibited the typical rolling behavior that was specific to E-selectin-conjugated region. No cell adhesion was observed on the regions that were not functionalized with E-selectin. MCF-7 cells exhibited faster rolling velocity (4.23 µm/s) as compared to HL-60 cells (2.12 µm/s). Note that the free flow on the wall should be 80 µm/s at 0.32 dyn/cm2, indicating that the speed of rolling cells was significantly reduced, as compared to non-interacting cells. Furthermore, it was observed that not all MCF-7 cells showed rolling. This is likely due to the CD24− subpopulation, indicating that this technology can also be used as a separation tool for the two subpopulations (CD24+ and CD24−) of the cells without modification steps, such as cell labeling.

Figure 10A:
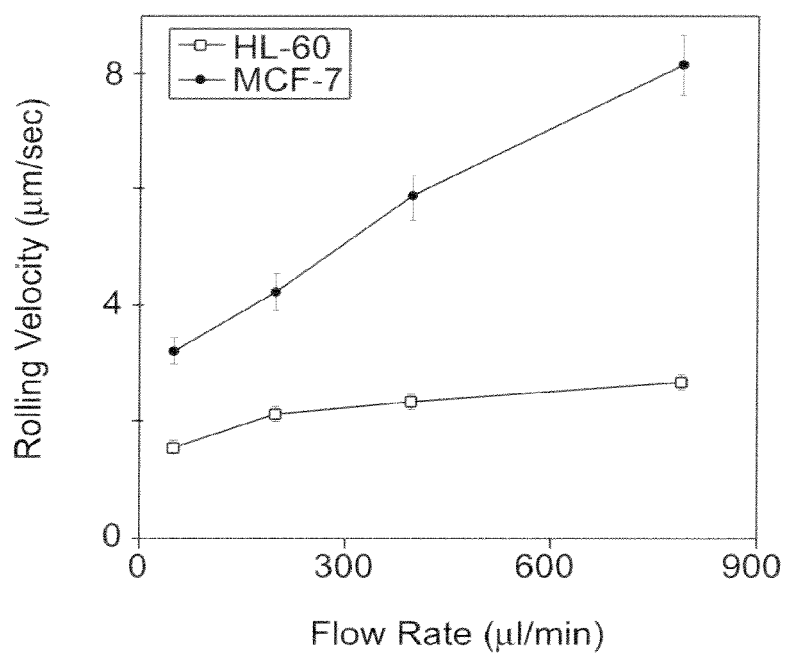
FIG. 10A is a graph illustrating the rolling velocity of HL-60 and MCF-7 cells on E-selectin coated surfaces at four different flow rates (50, 200, 400, and 800 µl/min).
Figure 10B:
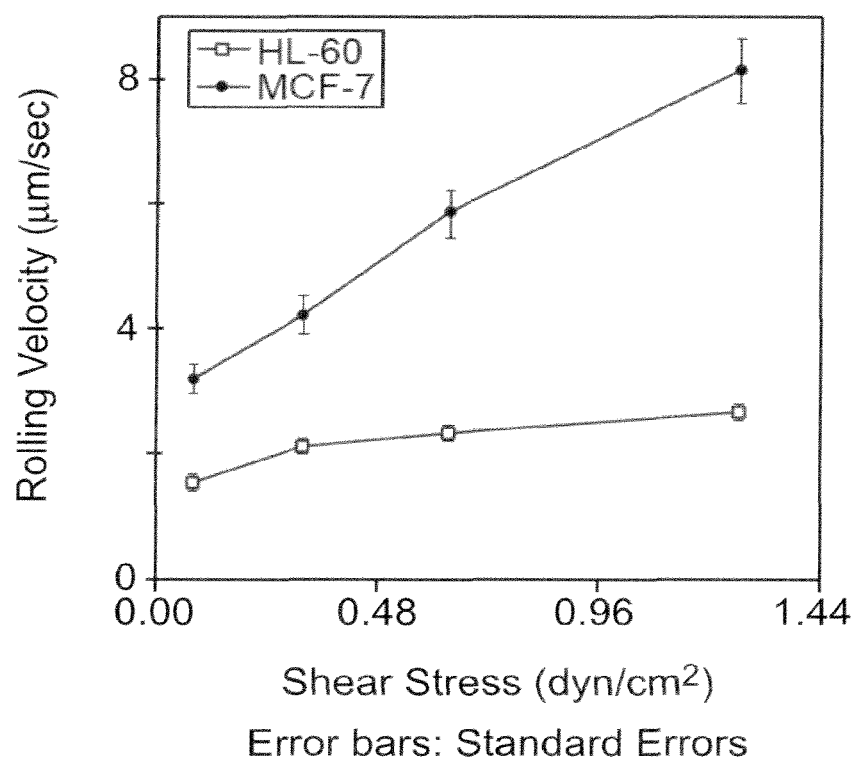
FIG. 10B is a graph illustrating the rolling velocity of HL-60 and MCF-7 cells on E-selectin coated on surfaces at four different shear stresses (0.08, 0.32, 0.64, and 1.28 dyn/cm$^2$), which correspond to the flow rates of FIG. 6A.

The rolling velocities of HL-60 and MCF-7 cells were measured at 4 different flow rates and corresponding shear stresses as plotted in FIGS. 10A and 10B, respectively. Note that the rolling velocity of MCF-7 cells was significantly increased with an increase of the flow rate (shear stress) whereas the rolling response of HL-60 cells was not as dependent upon the flow rate change.

Example 4: Tumor Cell Specific Capturing Using Anti-EpCAM

Surface preparation and the flow chamber experiments: The anti-EpCAM coated surfaces were prepared using a similar protocol that is described above. Instead of E-selectin, 5 µg/mL of anti-EpCAM was incubated on the Epoxy group functionalized glass slides (SuperEpoxy®, ArrayIt Inc, Sunnyvale, Calif.).

Figure 11:
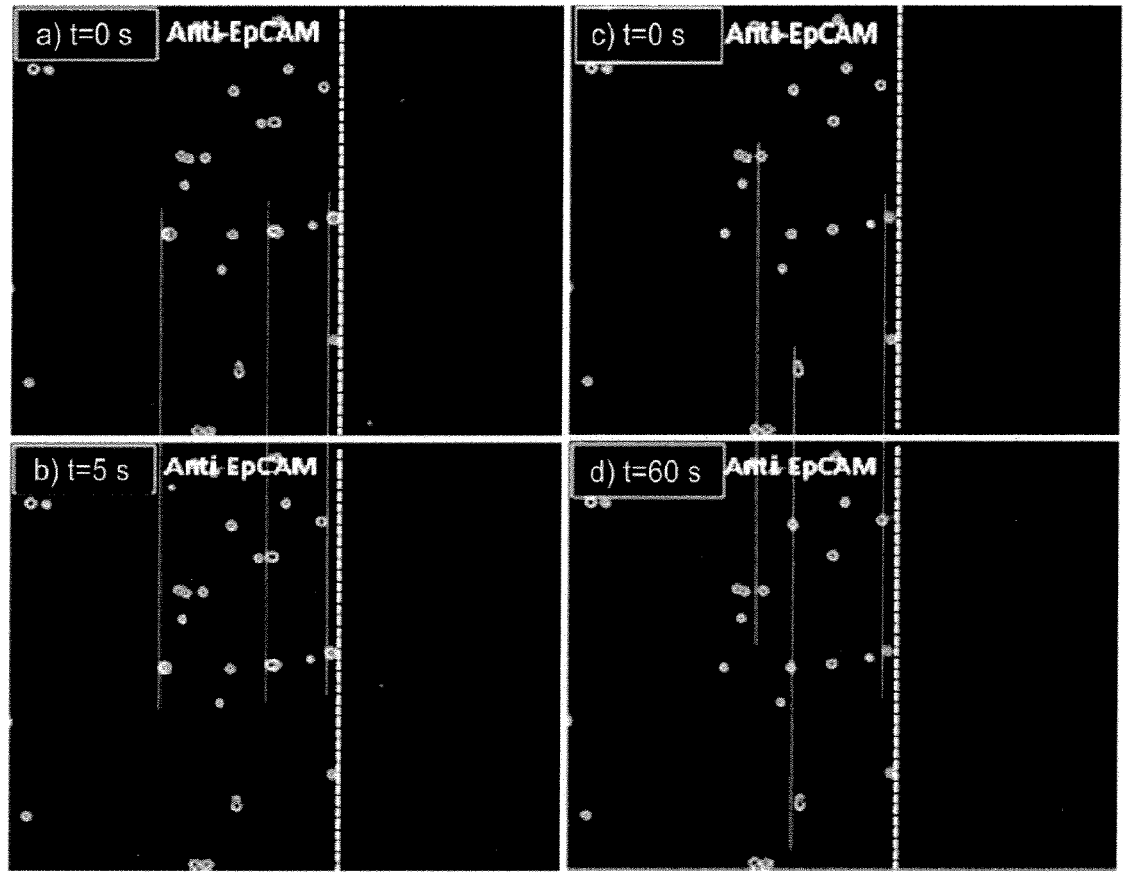
FIG. 11 are time-course images of MCF-7 cells on anti-EpCAM coated surfaces under shear stress of 0.32 dyn/cm$^2$. a) and b): time interval is 5 seconds. c) and d): time interval is 60 seconds. Note that MCF-7 cells were stationary adhered on anti-EpCAM coated region but very slowly moving on the surface (>3 µm/min).

As shown in FIG. 11, MCF-7 cells were captured on the anti-EpCAM coated region. HL-60 cells (used as a leukocyte model) did not interact with the surface functionalized with anti-EpCAM (data not shown).

Figure 12:
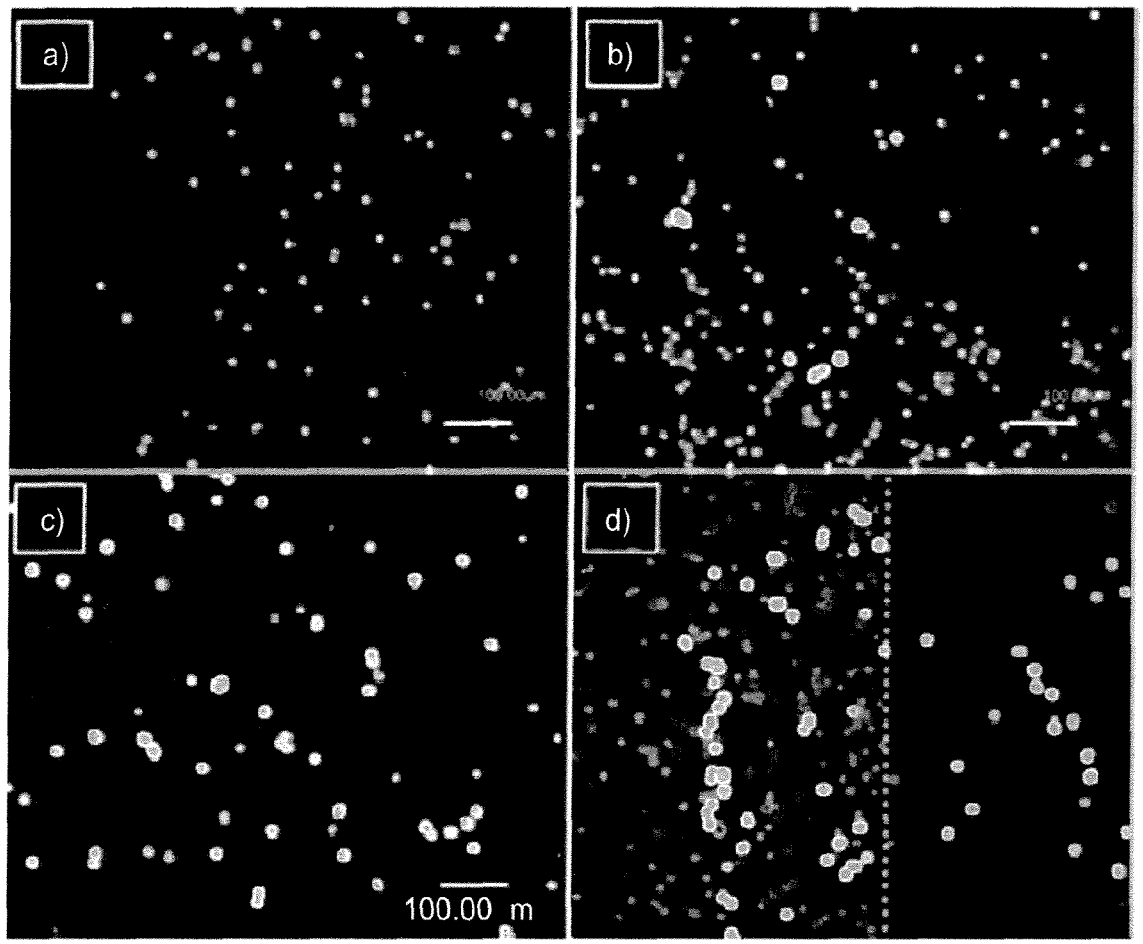
FIG. 12 are images of HL-60 and DsRED-transfected MCF-7 cells (red cells) on a) P-selectin, b) E-selectin, c) anti-EpCAM, and d) patterned E-selectin/anti-EpCAM coated surfaces, under shear stress of 0.32 dyn/cm$^2$. The patterned surface with E-selectin and anti-EpCAM (d) achieved efficient isolation of DsRED-transfected MCF-7 (a CTC model) cells from the mixture with HL-60 (a leukocyte model), on the anti-EpCAM coated region.

Example 5: Enhanced Separation of Cancer Cells Using Combination of Anti-EpCAM and E-Selectin To demonstrate the enhancement of separation efficiency of tumor cells through mimicking the naturally occurring process of cell rolling and multivalent effects, mixture of the two cell lines under flow was observed on the various surfaces functionalized by P-selectin, E-selectin, anti-EpCAM, and E-selectin/anti-EpCAM combination (FIG. 12). For easier recognition from the cell mixture, MCF-7 cells were transfected using HIV-1-based lentiviral vector and Discosoma sp. Red fluorescent protein (DsRED)-transfected MCF-7 (DsRED-MCF-7) cells were isolated from non-transfected cells prior to the flow chamber experiments. P-selectin (FIG. 12a) induced rolling of HL-60 but no interaction with DsRED-MCF-7 cells was observed. As expected from FIG. 5, E-selectin, on the other hand, caused both cell types to roll as presented in FIG. 12b. The anti-EpCAM coated surface induced stationary adhesion of DsRED-MCF-7 cells exclusively (FIG. 12c). The combination of E-selectin and anti-EpCAM provided separation of pure MCF-7 population from HL-60 and MCF-7 mixture on the anti-EpCAM immobilized region (the right-hand side) as shown in FIG. 12d. This result indicates that iterative rolling and stationary binding using combination of E-selectin and anti-EpCAM may enhance the separation capability of the surface, as compared to the surfaces functionalized with one of the two proteins alone.

Example 6: Enhanced Capturing Efficiency of Anti-EpCAM-Functionalized Surfaces with Addition of E-Selectin The enhanced separation efficiency observed in FIG. 12 was further supported by a quantitative analysis of capturing efficiency of the various surfaces. The surfaces were prepared as follows: the mixtures of anti-EpCAM and E-selectin at different composition ratios were prepared using the protocols described earlier. After placing a home-made gasket made of polydimethylsiloxane (PDMS) (one panel: 10 mm (L)×25 mm (W)) on the epoxy-functionalized glass substrate, 300 µl of mixtures were added and incubated for 4 hrs at RT. DsRED-MCF-7 cells were used again to easily distinguish the cells of interest from cell debris. Number of captured cells was counted using a microscope (Olympus IX70 inverted microscope) at each cycle, which was composed of forward flow (from left to right) for 2.5 min, and backward flow (from right to left) for 2.5 min at a flow rate of 100 µl/min that is correspondent to a shear stress of 0.16 dyn/cm$^2$. As the fixed number of DsRED-MCF-7 cells were perfused into the flow chamber, the number of the captured cells could be translated into the capturing efficiency (%).

Figure 13:
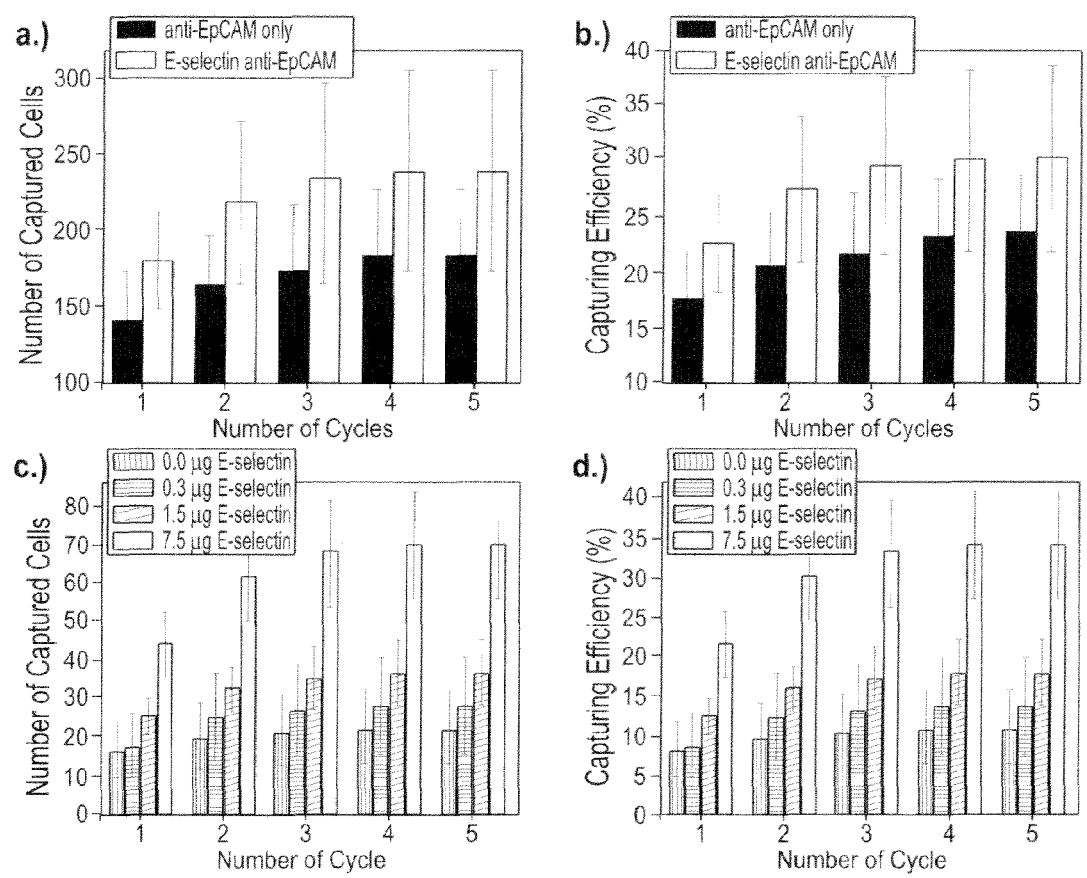
FIG. 13 are graphs illustrating the a) number of captured cells and b) capturing efficiencies of the surfaces immobilized with the mixtures of anti-EpCAM and E-selectin at various composition ratios (c) and d)). The number of DsRED-MCF-7 cells on each surface was counted and the capturing efficiency was calculated based on the total number of the MCF-7 cells injected into the flow chamber. The flow experiments were performed at the shear stress of 0.16 dyn/cm2. The average capturing efficiency of the surfaces with mixture of E-selectin and anti-EpCAM were generally higher than those with anti-EpCAM only. With an increase of added concentrations of E-selectin, the capturing efficiency of the surfaces was further enhanced. Error bars: standard error.

FIGS. 13a and 13b demonstrate enhanced capturing efficiency with the surface immobilized with mixture (anti EpCAM:E-selectin=1:1) as compared to the surface with anti EpCAM only. Furthermore, as shown in FIGS. 13c and 13d, the average number of captured cells and average capturing efficiency of the surfaces with the two proteins was enhanced as the concentration of E-selectin was increased. Taken together, the combination of E-selectin, which induces rolling of various cell types, and anti-EpCAM, which recognizes/captures tumor cells, greatly enhances the capturing of the cells, most likely because E-selectin-induced tumor cell rolling maximizes the chance of the tumor cells interacting with anti-EpCAM on the surface, resulting in the enhanced capturing efficiency. The isolation efficiency of the surface is further enhanced by incorporating microfluidic channels that induce rotation of flow, which is described below.

Example 7: Generating Defined Microdomains

Figure 14:
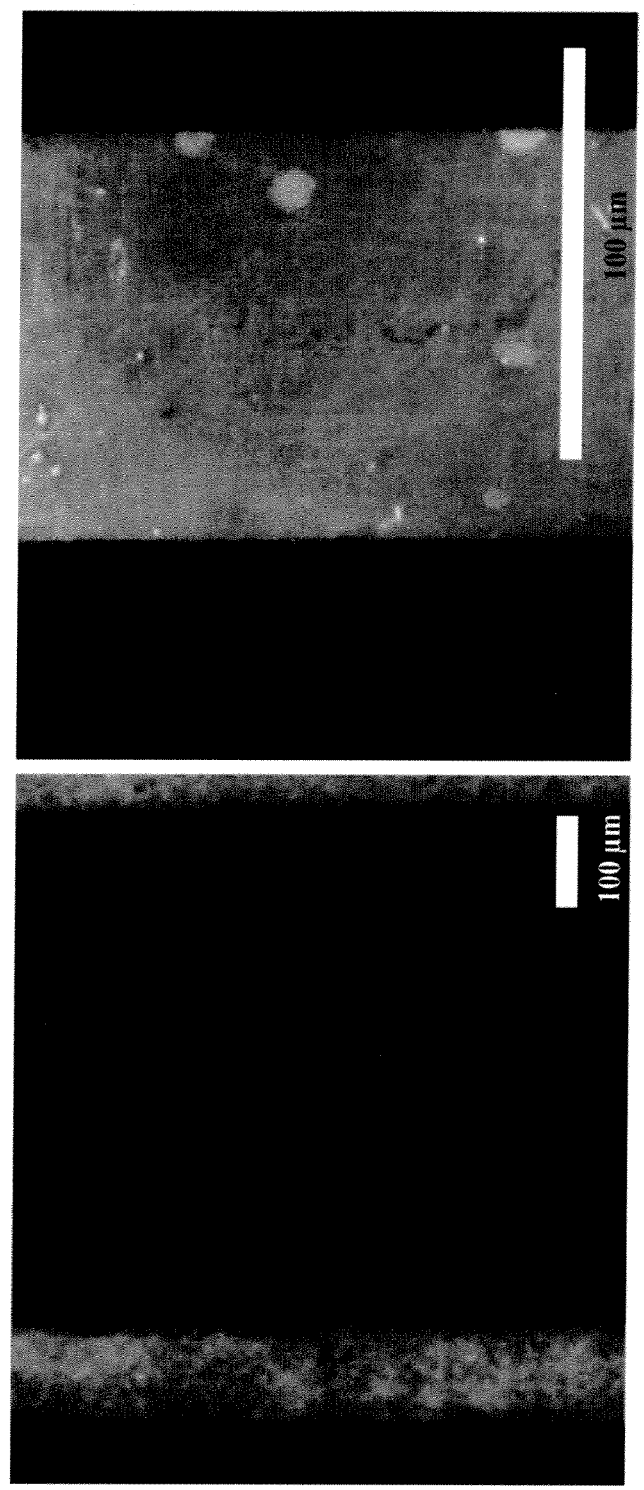
FIG. 14 is a fluorescent image of a micropatterned fluorescently labeled albumin formed by plasma ablation.

Plasma Ablation: A simple 100 µm wide line of Albumin was micropatterned onto a glass substrate using plasma ablation. Briefly, fluorescently labeled albumin was adsorbed onto a coverglass substrate at a pH of 7.4 for two hours. After this, a PDMS etch mask was placed onto the dried surface with PDMS covering regions 100 µm wide, spaced every 1000 µm. After exposure to an oxygen plasma at 100 W for 2 minutes, the mask was removed and the substrate was imaged as shown in FIG. 14. This technique can be extended to micropatterning domains of selectins and anti-EpCAM by first patterning the lines of anti-EpCAM similar to how the albumin was patterned, followed by backfilling with E-selectin to adsorb to the remaining surfaces. Additionally, plasma ablation will work to pattern covalently immobilized ligands in a similar matter as the oxygen plasma is very reactive and will oxidize and effectively burn up any organic molecule in contact with the plasma. For work in this project, either physisorption or plasma ablation is used, however it is important to note both require stencils and are similar techniques.

Microfluidic Adsorption: Micropatterns of EpCAM and E-Selectin can also be generated by using a microfluidic device 10 that can be placed onto a glass substrate. The desired surface molecules placed in soluble media and are injected through the microfluidic channels. Then the injection is stopped and the solution is allowed to adsorb to the surface over several hours. After this, the microfluidic network is peeled off and the desired micropattern is achieved. This technique is advantageous when the desired molecules are damaged by the heat generated during plasma ablation.

Example 8: Immobilization of Anti-EpCAM Through Polymeric Nanolinkers

Figure 15:
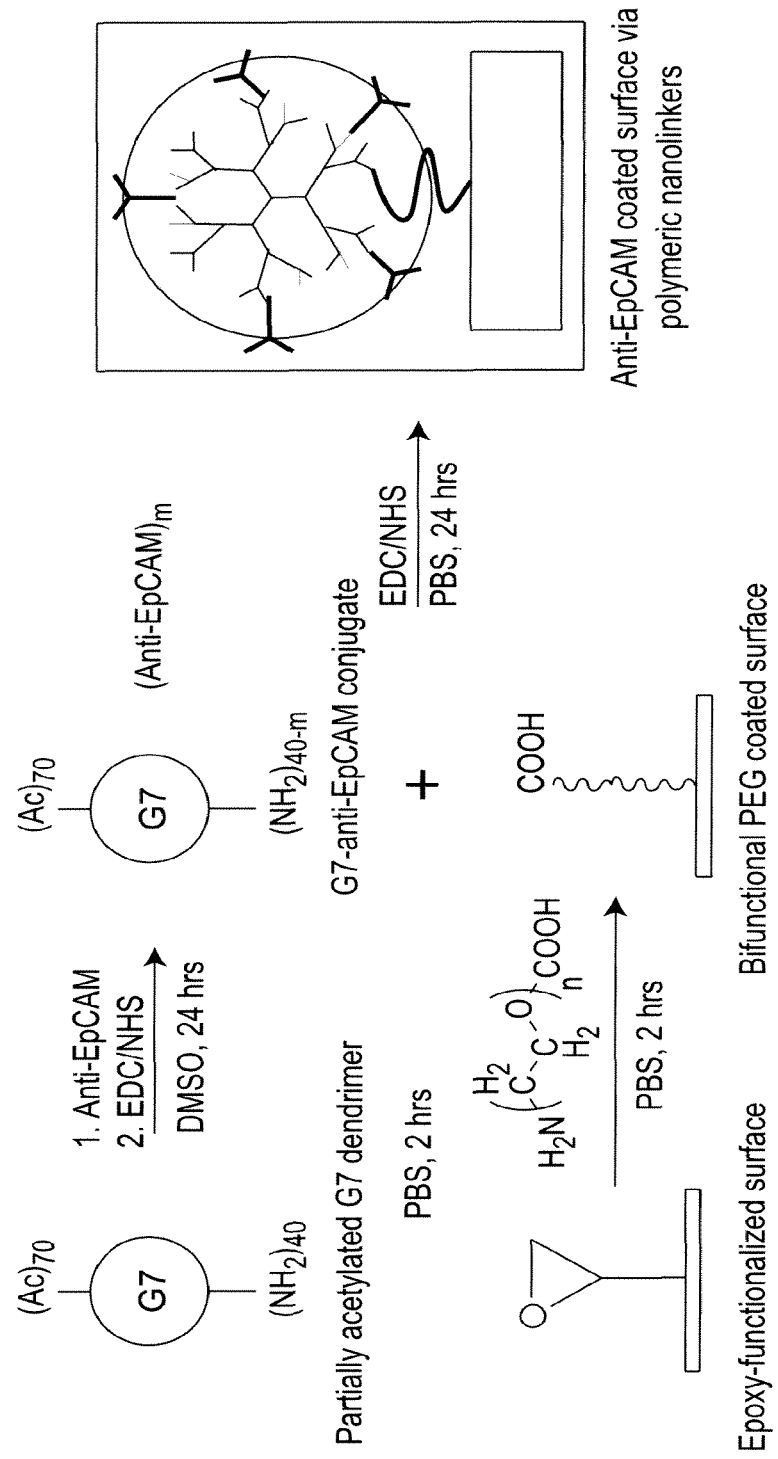
FIG. 15 is a schematic illustration of immobilization of anti-EpCAM via polymeric nanolinkers. Anti-EpCAM will be conjugated with G7 PAMAM dendrimer, followed by covalent immobilization on PEGylated surface. The local concentration of anti-EpCAM will be substantially increased by dendrimer that is flexible enough to be deformed to allow a maximal number of binding events to occur simultaneously in a small area.
Figure 16:
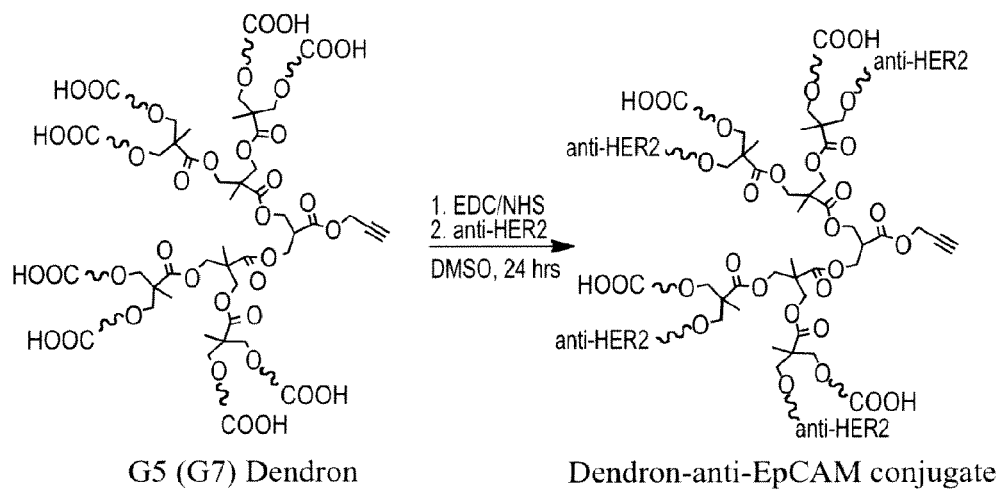
FIG. 16 is a schematic illustration of conjugation between polyester-64-carboxylate-1-alkyne dendron (dendron) and anti-EpCAM and immobilization of the conjugate to the surface through a PEG linker. Anti-EpCAM will be first conjugated with G6 polyester dendron, followed by covalent immobilization on PEGylated surface. The terminal carboxylic acid groups will provide reactive sites for anti-EpCAM and the alkyne group in the core will allow controlled immobilization on the PEGylated surface through click chemistry (i.e. only one PEG chain will be conjugated to the dendron conjugate). Note that G3 dendron is used in the figure for better illustration but G6 dendron that has 64 carboxylate groups will be actually employed.
Figure 16:
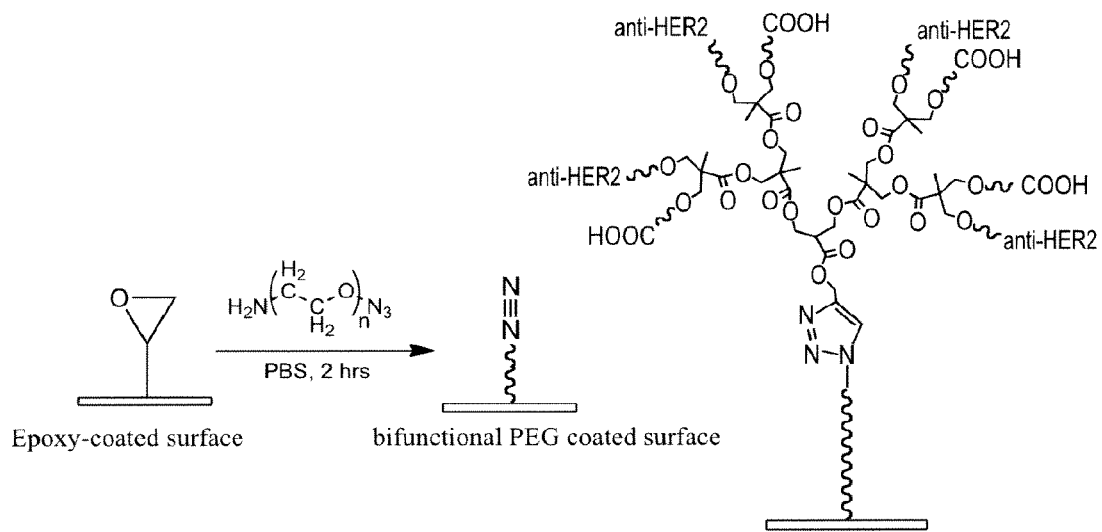

The surface is functionalized with anti-EpCAM coated domains via a polymeric nanolinker. The nanolinkers are composed of PAMAM dendrimers and PEG, dendron and PEG, and other linear polymers. An example of the immobilization process of anti-EpCAM is outlined in FIG. 15. For an enhanced multivalent effect, G7 PAMAM dendrimers (Sigma-Aldrich, St. Louis, Mo.) were partially acetylated and conjugated with multiple number of anti-EpCAM molecules, which increases the local concentration of anti-EpCAM that facilitates the multivalent binding between the surface and cells. The resulting dendrimer-anti-EpCAM conjugates were immobilized on the PEGylated surface through amide bond formation. A variety of parameters can be tested such as PEG chain length, size of dendrimer, number of conjugated anti-EpCAM, and degree of acetylation, in order to determine an optimal condition for various purposes.

In addition to the use of a PAMAM dendrimer as a component of the nanolinker, polyester-64-carboxylate-1-alkyne dendron (dendron) can also be used. Dendron has an advantage as it can use click chemistry for immobilization on the PEGylated surface and use amine (or carboxyl) based chemistries for conjugation with anti-EpCAM (and other biomarkers specific to cancer).

Example 9: Fabrication of a Biomimetic Microfluidic Chip

The microfluidic device 10 was fabricated in two steps. First, the cell capture surface 12 was prepared forming microdomains of the cell rolling-inducing agent and the capturing agent 18 on a glass substrate 14. Anti-EpCAM-dendrimer conjugates for CTC binding and was used by the capturing agent 18. The Anti-EpCAM was surrounded by E-Selectin, which was used as the cell rolling-inducing agent. Following this, a PDMS based microfluidic channel have a flow modification disposed on the ceiling was attached to the micropatterned substrate.

The capturing agent 18 was fabricated using a PDMS stencil. The PDMS stencil was formed using previously described and are well established procedures. Briefly, the microchannel layout was designed in AutoCAD and printed onto a high resolution (5080 dpi) transparency. This transparency was used as a photomask to selectively crosslink a photoresist which was spin coated onto a silicon wafer at a desired thickness (the spin velocity and time dictate the thickness). Following exposure, the unexposed, uncrosslinked photoresist was washed away, resulting in a negative mold of the desired device 10 structure. Next, PDMS is poured on to the negative mold and cured. Following curing, the PDMS stencil is peeled from the mold master and ready for use. As shown in FIG. 3, the stencil contains a micropatterned surface with features protruding from the surface, such that when the features contact the substrate 14, regions of the substrate 14 covered by the PDMS features will be masked.

The PDMS stencil was applied to a glass substrate 14 to mask regions of the substrate 14. The capturing agent 18, Anti-EpCAM, was applied to the unmasked regions of the substrate 14. The PDMS stencil was then removed and the substrate 14 was backfilled with the cell rolling-inducing agent E-Selectin, thereby attaching the E-Selectin to the exposed portions of the substrate 14.

Flow rotation in the microfluidic device 10 is induced by integrating a flow modification surface 20 into the microfluidic channel. The flow modification surface 20 included a herringbone structure. Standard soft lithographic techniques like those used to fabricating the stencil for micropatterning the dendrimer-anti-EpCAM were used to form the herringbone structure flow modification surface 20. A dual height SU-8 photoresist was used to form the mold for the flow modification surface 20. This dual height SU8 mold was prepared by first spinning and patterning the microfluidic channel. Before the pattern was developed a second photoresist layer was spun onto the surface to generate a pattern for the herringbone shaped ridges 22 the flow modification surface 20. Alignment marks were added to the designs to facilitate proper orientation of the second photoresist layer. Following selective exposure and a second hard bake the entire wafer was developed and the resulting mold contained both the microchannel and structures for casting the ridges 22 of the flow modification surface 20. PDMS is then cast onto the mold to form a microchannel having a flow modification surface 20. The resulting microfluidic channel was then attached to the cell capture surface 12.

The dimensions of the microchannel and the flow modification surface 20 can be optimized to maximize fluid rotation while minimizing the fluidic resistance which is governed by the following equation:

$$R = \frac{12\mu L}{wh^3}$$

Where $\mu$ is the kinematic viscosity, L is the channel length, w is the channel width, and h is the channel height. In addition to the height and width of the microchannel, the dimensions of the herringbone ridges 22 can be optimized. Previous studies showed an optimal dimension of the herringbone ridges 22 to be a height h1 of 85 μm, a width w of 200 μm, a θ of 60 degrees, placement of the ridges ⅔ from one side. The ridges 22 have a thickness t of about 15 μm. Increasing rotations can increase the contact of cells to the cell capture surface 12.

Figure 17:
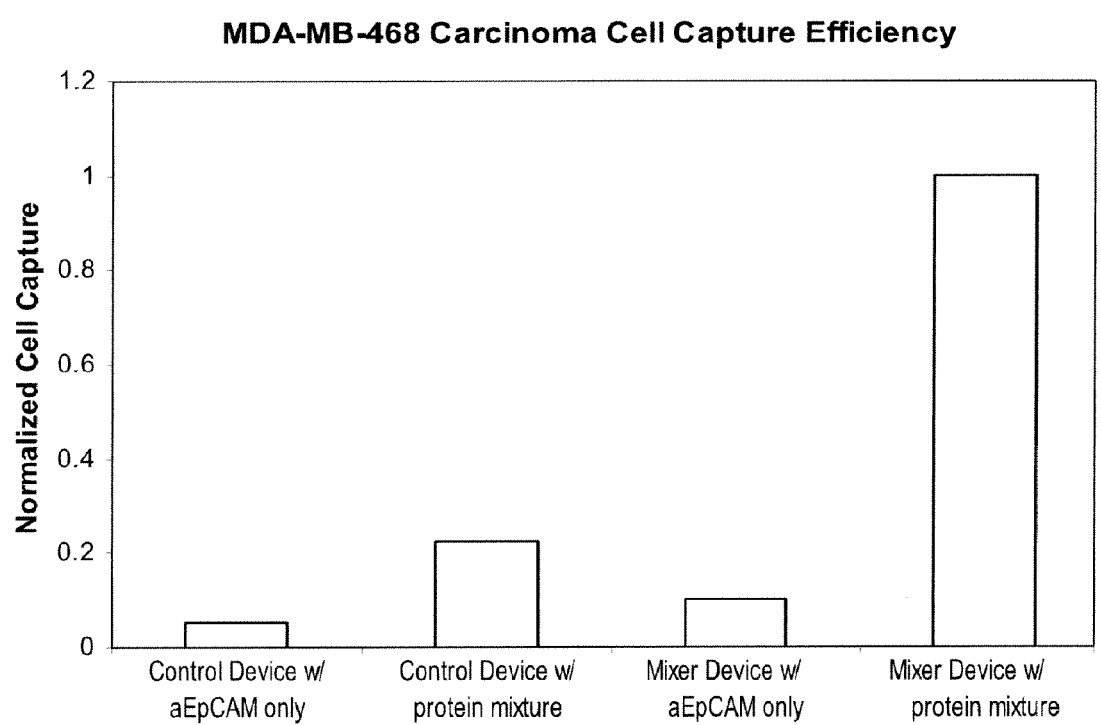
FIG. 17 is a graph illustrating the ability of anti-EpCAM- and E-selectin-functionalized microfluidic devices to capture circulating tumor cells. The mixer device induces a rotational flow through the channel while the control device does not. The mixer device with both anti-EpCAM- and E-selectin-functionalized surfaces captures circulating tumor cells significantly more efficiently than the mixer device with only anti-EpCAM or the corresponding control devices.

Example 10: Enhanced CTC Capture Efficiency is Provided by Microfluidic Devices that Induce Rotational Flow Polydimethylsiloxane and glass microfluidic devices were fabricated using soft-lithography. The glass bottom was coated with either adsorbed anti-EpCAM or a mixture of adsorbed anti-EpCAM and E-selectin, creating a cell capture surface 12. Control devices consisted of ten rectangular channels 45 mm long, 730 μm wide and 120 μm high. Additionally, microfluidic devices had 120 μm height slanted ridged ceiling structures as the flow modification surface 20. The flow modification surface 20 included 360 μm wide grooves and 110 μm wide ridges 22 aligned at 45 degree angles to the channel wall. These ceiling structures induce downward flows which carry cells downward toward the capture surface. These microfluidic devices, designed to isolate carcinoma cells from blood samples, were tested with a suspension of MDA-MB-468 breast adenocarcinoma cells in buffer solution. Cell suspensions were injected into the device 10 at a constant flow rate using a syringe pump with flow rates that corresponded to a shear stress of 0.5 dyn/cm$^2$ on the control channel floor. Five minutes after flow into the device 10 was started, a 865 μm×660 μm section of the device 10 was imaged at one frame per second for one minute. The total number of captured stationary cells and total cells in bulk flow were counted. To estimate capture efficiency, the total numbers of captured cells were divided by the number of cells in bulk flow entering the device 10 over one minute. The cell capture was then normalized to the maximum capture efficiency. The mean data for a total of three trials is shown in FIG. 17. The results indicate that the microfluidic device 10 having the flow modification surface 20 had significantly improved capture efficiency over the control device 10, and that the protein mixture devices had more cell capture than the devices with only anti-EpCAM immobilized on the capture surface.

What is claimed is:

1. A method of capturing a Circulating Tumor Cell (CTC) from a sample comprising the step of introducing said sample into a microfluidic device under conditions that allow a CTC to bind to a cell rolling-inducing agent and a capturing agent, the device comprising (i) an immobilized cell rolling-inducing agent, and (ii) an immobilized capturing agent, wherein the capturing agent is an antibody that specifically binds to a CTC and is immobilized via attachment to a modified poly(amidoamine) dendrimer covalently attached to the surface of the device and wherein the dendrimer organizes multiple capturing agents on the surface of the device to facilitate a multivalent effect.

2. The method of claim 1 further comprising applying a shear stress between 0.05 and 10 dyn/cm$^2$ on the sample introduced into the device.

3. The method of claim 2 wherein the shear stress is between 0.1 and 2.0 dyn/cm$^2$.

4. The method of claim 3 wherein the shear stress is about 0.16 dyn/cm$^2$.

5. The method of claim 1 wherein the cell rolling-inducing agent is a selectin or a CTC binding fragment of a selectin.

6. The method of claim 5 wherein the selectin is selected from the group consisting of E-selectin, P-selectin, and L-selectin.

7. The method of claim 1 wherein the antibody is one or more of anti-EpCAM, trastuzumab, bevacizumab, anti-CD33 antibody, anti-CD20 antibody and fragments thereof.

8. The method of claim 1 wherein the modified poly (amidoamine) dendrimer is selected from the group consisting of a generation 3, a generation 4, a generation 5, a generation 6, a generation 7, a generations 8, and a generation 9 modified poly(amidoamine) dendrimer.

9. The method of claim 1 wherein a linear polymer is attached to the surface of the device and the dendrimer is attached the linear polymer on the surface of the device.

10. The method of claim 9 wherein the linear polymer is poly(ethylene glycol).

11. The method of claim 1, wherein the immobilized cell rolling-inducing agent and the immobilized capturing agent are arranged in a substantially uniform manner.

12. The method of claim 1, wherein the immobilized cell rolling-inducing agent and the immobilized capturing agent are arranged in a pattern.

13. A microfluidic device for capturing a Circulating Tumor Cell (CTC) from a sample, comprising:
a channel comprising a cell capture surface and a flow modification surface,
wherein the cell capture surface comprises a cell rolling-inducing agent and a capturing agent immobilized on the cell capture surface, wherein the capturing agent is an antibody that specifically binds to a CTC and is immobilized via attachment to a modified poly(amidoamine) dendrimer covalently attached to the surface of the device and wherein the dendrimer organizes multiple capturing agents on the surface of the device to facilitate a multivalent effect.

14. The device of claim 13, wherein the cell rolling-inducing agent is a selectin or a CTC binding fragment of a selectin.

15. The device of claim 13, wherein the antibody is one or more of anti-EpCAM, trastuzumab, bevacizumab, anti-CD33 antibody, anti-CD20 antibody and fragments thereof.

16. The device of claim 13 wherein the modified poly (amidoamine) dendrimer is selected from the group consisting of a generation 3, a generation 4, a generation 5, a generation 6, a generation 7, a generations 8, and a generation 9 modified poly(amidoamine) dendrimer.

17. The device of claim 13 wherein a linear polymer is attached to the surface of the device and the dendrimer is attached to the linear polymer on the surface of the device.

18. The device of claim 17 wherein the linear polymer is poly(ethylene glycol).

19. The device of claim 13, wherein the immobilized cell rolling-inducing agent and the immobilized capturing agent are arranged in a substantially uniform manner.

20. The device of claim 13, wherein the immobilized cell rolling-inducing agent and the immobilized capturing agent are arranged in a pattern.

* * * * *

UNITED STATES PATENT AND TRADEMARK OFFICE
CERTIFICATE OF CORRECTION

PATENT NO. : 9,964,541 B2  
APPLICATION NO. : 15/016005  
DATED : May 8, 2018  
INVENTOR(S) : Seungpyo Hong et al.

Page 1 of 1

It is certified that error appears in the above-identified patent and that said Letters Patent is hereby corrected as shown below:

On the Title Page

Item [*], Line 3, "0 days. days." should be -- 0 days. --.

Signed and Sealed this  
Second Day of October, 2018

Andrei Iancu  
*Director of the United States Patent and Trademark Office*